(12) United States Patent
Hanafusa et al.

(10) Patent No.: US 8,076,129 B2
(45) Date of Patent: *Dec. 13, 2011

(54) REACTOR PLATE AND REACTION PROCESSING METHOD

(75) Inventors: Nobuhiro Hanafusa, Kyoto (JP); Koretsugu Ogata, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 540 days.

This patent is subject to a terminal disclaimer.

(21) Appl. No.: 12/179,463

(22) Filed: Jul. 24, 2008

(65) Prior Publication Data

US 2009/0029422 A1    Jan. 29, 2009

(30) Foreign Application Priority Data

Jul. 26, 2007  (JP) ................................. 2007-194717
Aug. 31, 2007  (JP) ................................. 2007-226177

(51) Int. Cl.
*C12M 1/00* (2006.01)
*C12M 3/00* (2006.01)

(52) U.S. Cl. .................................. 435/289.1; 435/91.2

(58) Field of Classification Search ................. 435/91.2, 435/165, 289.1; 422/52, 68.1, 82.05, 82.08, 422/129
See application file for complete search history.

(56) References Cited

U.S. PATENT DOCUMENTS

| | | | | |
|---|---|---|---|---|
| 6,391,623 B1 * | 5/2002 | Besemer et al. | ............ | 435/287.2 |
| 2009/0042256 A1 * | 2/2009 | Hanafusa et al. | ............ | 435/91.2 |

FOREIGN PATENT DOCUMENTS

| | | |
|---|---|---|
| JP | 3452717 B2 | 7/2003 |
| JP | 2004-163104 A | 6/2004 |
| JP | 2005-114430 A | 4/2005 |
| JP | 2005-177749 A | 7/2005 |

* cited by examiner

*Primary Examiner* — William H Beisner
*Assistant Examiner* — Michael Hobbs
(74) *Attorney, Agent, or Firm* — Cheng Law Group, PLLC

(57) ABSTRACT

The reactor plate preferably includes a sealed reactor, a reactor flow channel connected to the reactor, a sample container constituted from a sealed container provided separately from the reactor, a sample container flow channel to be connected to the sample container, a syringe for sending a liquid, a switching valve for connecting the syringe to the reactor flow channel or the sample container flow channel, and a projecting flow channel connected to the end of the sample container flow channel located on the sample container side. The sample container has a penetrable portion through which the projecting flow channel can penetrate and which is provided to be opposed to the projecting flow channel and is located such that the projecting flow channel penetrating the penetrable portion is brought into contact with a liquid contained in the sample container. The sample container can be connected to the sample container flow channel.

23 Claims, 13 Drawing Sheets

REACTOR PLATE AND REACTION PROCESSING METHOD

BACKGROUND OF THE INVENTION

1. Field of the Invention

The present invention relates to a reactor plate suitable for use in various analyses such as biological analyses, biochemical analyses and general chemical analyses in the fields of medical care and chemistry, and a reaction treatment method for treating such a reactor plate.

2. Description of the Related Art

As small-size reaction apparatuses for use in biochemical analyses and general chemical analyses, micro multi-chamber apparatuses are known. Examples of such micro multi-chamber apparatuses include microwell reactor plates such as microtiter plates constituted from a flat substrate having a plurality of wells in the surface thereof (see, for example, Japanese Patent Application Laid-open No. 2005-177749).

Further, as a structure for quantitatively treating a trace amount of liquid, there is proposed a trace amount liquid dispensing structure having a first flow channel, a second flow channel, a third flow channel which opens into the flow channel wall of the first flow channel, and a fourth flow channel which opens into the flow channel wall of the second flow channel and connects one end of the third flow channel to the second flow channel and which is relatively less likely to cause capillary attraction than the third flow channel and is narrower than the other three channels (see, for example, Japanese Patent Application Laid-open Nos. 2004-163104 and 2005-114430). When such a trace amount liquid dispensing structure is used, a liquid is introduced into the first flow channel and drawn into the third flow channel, and then the liquid remaining in the first flow channel is removed, and next the liquid having a volume corresponding to the capacity of the third flow channel is dispensed into the second flow channel.

In the case of a conventional microwell reactor plate, the upper surface of the reactor plate is exposed to the atmosphere during use. Therefore, there is a fear that foreign matter will enter a sample from the outside, or on the other hand, there is a case where a reaction product will pollute an environment outside the reactor plate.

Also in the case of the trace amount liquid dispensing structure disclosed in Japanese Patent Application Laid-open No. 2004-163104 or 2005-114430, each of the first flow channel and the second flow channel has, at both ends thereof, liquid introduction ports exposed to the atmosphere, and therefore there is a case where a reaction product will leak through the ports and then pollute an environment outside the structure.

SUMMARY OF THE INVENTION

It is an object of the present invention to provide a reactor plate capable of preventing the entry of foreign matter from the outside and the pollution of a surrounding environment, and a reaction treatment method using the reactor plate.

The reactor plate according to the present invention includes a sealed reactor, a reactor flow channel connected to the reactor, a sealed container which is provided separately from the reactor and contains a liquid, a sealed container flow channel to be connected to the sealed container, a syringe for sending a liquid, a switching valve for connecting the syringe to the reactor flow channel or the sealed container flow channel, and a projecting flow channel connected to the end of the sealed container flow channel located on the sealed container side. The sealed container has a penetrable portion through which the projecting flow channel can penetrate and which is provided to be opposed to the projecting flow channel and is located at such a position that the projecting flow channel penetrating the penetrable portion is brought into contact with a liquid contained in the sealed container. Therefore, the sealed container can be connected to the sealed container flow channel by inserting the tip of the projecting flow channel into the sealed container through the penetrable portion.

In the reactor plate according to the present invention, the reactor and the sealed container are sealed, and a liquid contained in the sealed container can be injected into a main flow channel using the syringe and the switching valve. This makes it possible to prevent the entry of foreign matter from the outside of the reactor plate and the leakage of the liquid from the reactor plate, thereby preventing the pollution of an environment outside the reactor plate. Particularly, in a case where the reactor plate according to the present invention is intended for use in measuring a gene-containing sample, there is a great advantage that the sample can be treated in a closed system.

Further, the reactor plate according to the present invention can be stored with the sealed container being separated from the sealed container flow channel. In a case where the sealed container containing a liquid such as a reagent or dilution water or a powdered solid such as a reagent is connected to the sealed container flow channel during storage, there is a fear that the liquid or solid will flow into the sealed container flow channel. However, as described above, since the reactor plate according to the present invention can be stored with the sealed container being separated from the sealed container flow channel, such a fear can be eliminated.

Further, as described above, since the reactor plate according to the present invention can be stored with the sealed container being separated from the sealed container flow channel, it is possible, even when the sealed container previously contains a liquid, to prevent the liquid contained in the sealed container from evaporating through the sealed container flow channel during storage. In a case where the liquid previously contained in the sealed container is a reagent, it is possible to prevent the reagent from being concentrated.

Further, by establishing connections between the sealed container and the sealed container flow channel, and between the syringe and the sealed container flow channel through the switching valve, it is possible to connect the sealed container to the syringe through the sealed container flow channel and the switching valve. In this flow channel connection state, by allowing the syringe to suck and discharge a liquid contained in the sealed container, it is possible to stir the liquid. As described above, since a liquid can be stirred using the sealed container, the reactor plate according to the present invention does no need to have a container intended only for stirring a liquid or a stirring portion. This makes it possible to eliminate the necessity to provide a space for arranging a container intended only for stirring a liquid or a stirring portion, thereby reducing the size of the reactor plate as compared to a case where a container intended only for stirring a liquid or a stirring portion is provided. However, the reactor plate according to the present invention may have a container intended only for stirring a liquid or a stirring portion. It is to be noted that in the reactor plate according to the present invention, a liquid to be fed to the reactor is stirred not only in the sealed container but also in the flow channel and the syringe by sucking and discharging the liquid into and from the syringe.

The reactor plate according to the present invention may include two or more sets of the sealed container, the sealed container flow channel, and the projecting flow channel. In this case, the switching valve can connect the syringe to any of the sealed container flow channels, and the two or more separate sealed containers can previously contain different liquids or powdered solids. This makes it possible to allow dilution water and a reagent to be contained in different sealed containers or to allow two or more kinds of reagents to be contained in different sealed containers, thereby expanding the application range of the reactor plate. Further, as described above, since each of the sealed containers can be connected to the syringe through the sealed container flow channel and the switching valve, a liquid contained in each of the sealed containers can be stirred therein.

The reactor plate according to the present invention may also include a sealed container holding system for holding the sealed container at a first holding position so that the penetrable portion and the projecting flow channel are opposed to each other and at a second holding position so that the tip of the projecting flow channel is inserted into the sealed container through the penetrable portion. In this case, the sealed container can be held at the first holding position during the storage of the reactor plate, and can be shifted to the second holding position to connect the sealed container to the sealed container flow channel before the use of the reactor plate to make the reactor plate available.

The reactor plate according to the present invention may further include a sealed container air drain flow channel to be connected to the sealed container and a second projecting flow channel connected to the end of the sealed container air drain flow channel located on the sealed container side, wherein the sealed container may further have a second penetrable portion through which the second projecting flow channel can penetrate and which is provided to be opposed to the second projecting flow channel and is located at such a position that the second projecting flow channel penetrating the second penetrable portion is inserted into a space in the sealed container but is not brought into contact with a liquid contained in the sealed container. In this case, by inserting the tip of the second projecting flow channel into the sealed container through the second penetrable portion, an air space in the sealed container is connected to the sealed container air drain flow channel. This makes it possible to move a gas between the sealed container and the sealed container air drain flow channel when a liquid is injected into or sucked from the sealed container and thereby to smoothly inject and suck the liquid into and from the sealed container.

In a case where the reactor plate according to the present invention includes the sealed container air drain flow channel, the sealed container may further have a sealed container air drain space which is provided separately from a sealed container main space having the penetrable portion through which the projecting flow channel of the sealed container flow channel can penetrate, and which serves as an air space to be connected to the sealed container air drain flow channel. In this case, a communicating flow channel is provided at a position higher than the level of a liquid contained in the sealed container main space in order to provide communication between the sealed container main space and the sealed container air drain space. The sealed container main space is connected to the sealed container air drain flow channel through the communicating flow channel by inserting the tip of the second projecting flow channel into the sealed container air drain space through the second penetrable portion before the use of the reactor plate. This makes it possible to move a gas between the sealed container main space and the sealed container air drain flow channel when a liquid is injected into or sucked from the sealed container main space and thereby to smoothly inject and suck the liquid into and from the sealed container main space.

The inner diameter of the sealed container air drain space is preferably 3 mm or less. By allowing the sealed container air drain space to have an inner diameter as small as 3 mm or less, it is possible, even when, for example, a liquid contained in the sealed container main space flows into the sealed container air drain space through the communicating flow channel before the sealed container is connected to the sealed container flow channel and to the sealed container air drain flow channel, to easily return the liquid, which has flown into the sealed container air drain space through the communicating flow channel, into the sealed container main space by connecting the sealed container main space to the syringe and operating the syringe in its suction direction.

The reactor plate according to the present invention may include two or more sets of the sealed container, the sealed container flow channel, the projecting flow channel, the sealed container air drain flow channel, and the second projecting flow channel. In this case, the switching valve can connect the syringe to any of the sealed container flow channels, and the two or more separate sealed containers can previously contain different liquids or powdered solid. This makes it possible to allow dilution water and a reagent to be contained in different sealed containers and to allow two or more kinds of reagents to be contained in different sealed containers, thereby expanding the application range of the reactor plate.

The reactor plate according to the present invention may further include a sealed container holding system for holding the sealed container at a first holding position so that the penetrable portion and the projecting flow channel are opposed to each other and the second penetrable portion and the second projecting flow channel are opposed to each other and at a second position so that the tip of the projecting flow channel is inserted into the sealed container through the penetrable portion and the tip of the second projecting flow channel is inserted into the sealed container through the second penetrable portion. In this case, the sealed container can be held at the first holding position during the storage of the reactor plate, and can be shifted to the second holding position to connect the sealed container to the sealed container flow channel and the sealed container air drain flow channel before the use of the reactor plate to make the reactor plate available. This makes it possible to smoothly inject and suck a liquid into and from the sealed container.

The sealed container may include a sample container for receiving a sample liquid. This eliminates the necessity to separately provide a container for receiving a sample.

The sample container may have an upper opening hermetically sealed with an elastic member through which a sharp-tipped dispensing tool can penetrate to form a through hole closable by pulling out the dispensing tool due to its elasticity. In this case, it is possible to inject a sample liquid into the sample container by allowing the tip of the dispensing tool to penetrate through the elastic member, and it is also possible to prevent the leakage of the sample liquid injected into the sample container to the outside of the sample container. Alternatively, the sample container may have an upper opening hermetically sealed with an elastic member having a cut openable by inserting a sample dispensing tool and closable by pulling out the sample dispensing tool due to its elasticity so that the upper opening can be hermetically sealed again. In this case, it is possible to prevent not only the leakage of a sample liquid to the outside of the sample container but also the occurrence of a problem that a trace amount of sample liquid as small as several microliters cannot be smoothly injected into the sample container due to an increase in the inner pressure of the sample container caused by insertion of the sample dispensing tool.

The sample container may previously contain a sample pretreatment solution or a reagent. This eliminates the necessity to dispense a sample pretreatment solution or a reagent into the sample container.

In a case where the reactor plate according to the present invention is intended for use in gene analyses, the reactor plate preferably includes a gene amplification container for carrying out gene amplification reaction, which is constituted from the sealed container. The gene amplification reactor preferably has a shape suitable for temperature control carried out according to a predetermined temperature cycle. Alternatively, the reactor may be used as a gene amplification portion. In this case, even when the amount of a gene contained as a measuring object in a sample liquid is very small, it is possible to amplify the gene by gene amplification reaction such as PCR or LAMP in the reactor plate, thereby improving analytical accuracy.

An example of the switching valve includes a rotary valve. By using a rotary valve having a port to be connected to the syringe at a rotational center thereof and by arranging the syringe on or above such a rotary valve, it is possible to shorten or eliminate a flow channel for connecting together the port and the syringe, thereby simplifying the structure of the reactor plate. Further, it is also possible to effectively use the space above the switching valve, thereby reducing the two-dimensional size of the reactor plate as compared to a case where the syringe is arranged in a space other than the space above the switching valve.

A specific example of the flow channel configuration of the reactor plate according to the present invention is as follows. For example, the reactor plate according to the present invention may further include a reactor air drain flow channel connected to the reactor, wherein the reactor flow channel is constituted from a groove formed in a contact surface between two substrates bonded together or from the groove and a through hole formed in the substrate, and has a main flow channel to be connected to the syringe, a measuring flow channel having a predetermined capacity and branching off from the main flow channel, and an injection flow channel whose one end is connected to the measuring flow channel and other end is connected to the reactor, and wherein the main flow channel and the reactor air drain flow channel are hermetically sealable, and the injection flow channel is narrower than the measuring flow channel and does not allow a liquid to pass through it under a liquid introduction pressure at which the liquid is introduced into the main flow channel and the measuring flow channel and under a purge pressure at which the liquid is purged from the main flow channel but allows the liquid to pass through it under a pressure higher than the liquid introduction pressure and the purge pressure. By providing the reactor air drain flow channel, it is possible to move a gas between the reactor and the reactor air drain flow channel when a liquid is injected into the reactor through the injection flow channel, thereby to smoothly inject the liquid into the reactor. Further, by providing the reactor air drain flow channel, it is also possible to inject a liquid into the reactor by using a method in which a gas is sucked from the reactor through the reactor air drain flow channel to reduce pressure in the reactor.

In this regard, it is to be noted that the phrase "the injection flow channel is narrower than the measuring flow channel" means that, when the injection flow channel is constituted from two or more flow channels, each of the two or more flow channels constituting the injection flow channel is narrower than the measuring flow channel.

The present invention is also directed to a reaction treatment method using the reactor plate according to the present invention. The reaction treatment method according to the present invention includes: filling the main flow channel and the measuring flow channel with a liquid under the liquid introduction pressure; allowing a gas to flow through the main flow channel to purge the liquid from the main flow channel while the liquid contained in the measuring flow channel is left as it is; and injecting the liquid contained in the measuring flow channel into the reactor through the injection flow channel by creating a positive pressure much higher than the liquid introduction pressure in the main flow channel, creating a negative pressure in the reactor, or creating a positive pressure in the main flow channel and a negative pressure in the reactor. According to the reaction treatment method of the present invention, it is possible to prevent entry of foreign matter from the outside of the reactor plate and leakage of a liquid to the outside of the reactor plate, thereby to prevent pollution of an environment outside the reactor plate.

The contact angle of a water droplet on the injection flow channel surface is preferably 90° or more, and the area of the interface between the injection flow channel and the measuring flow channel is preferably in the range of 1 to 10,000,000 $\mu m^2$. This makes it difficult for a liquid to enter the injection flow channel when the liquid is introduced into the main flow channel and the measuring flow channel, thereby making it possible to increase a liquid introduction pressure at which the liquid is introduced into the main flow channel and the measuring flow channel. In this regard, it is to be noted that when the injection flow channel is constituted from two or more flow channels, the phrase "area of the interface between the injection flow channel and the measuring flow channel" means the area of the interface between each of the two or more flow channels constituting the injection flow channel and the measuring flow channel.

The reactor plate according to the present invention may include the two or more reactors. In this case, the measuring flow channel and the injection flow channel may be provided for each of the reactors, and the two or more measuring flow channels may be connected to the main flow channel. This makes it possible to introduce a liquid into the two or more measuring flow channels one after another and then inject the liquid into the two or more reactors through the injection flow channels at the same time.

The other end of the injection flow channel may be located at the tip of a projection projecting from the upper surface of the reactor toward the inside of the reactor. In this case, the projection may have a proximal end and a distal end narrower than the proximal end. This makes it easy to drop a liquid into the reactor when the liquid is injected into the reactor through the injection flow channel.

The reactor may be used for carrying out at least any of color reaction, enzyme reaction, and fluorescence, chemiluminescence or bioluminescence reaction.

In a case where the reactor plate according to the present invention is intended for use in measuring a gene-containing sample, a sample having been subjected to gene amplification reaction may be introduced into the reactor plate, or a gene amplification reagent may be previously contained in or dispensed into the sealed container or the reactor of the reactor plate so that gene amplification reaction can be carried out therein.

Examples of the gene amplification reaction include PCR and LAMP. As for PCR for amplifying DNA, there is proposed a method for carrying out PCR directly from a sample such as blood without pretreatment. This method is a nucleic acid synthesis method for amplifying a target gene contained in a gene-containing sample by adding a gene-containing body contained in the gene-containing sample or the gene-containing sample itself to a gene amplification reaction liquid so that the pH of the obtained mixture is in the range of 8.5 to 9.5 (25° C.) (see Japanese Patent No. 3452717).

The reactor may be made of an optically-transparent material so that optical measurement can be carried out from the top or bottom side of the reactor. This makes it possible to optically measure a liquid contained in the reactor without transferring the liquid into another container.

In a case where a liquid to be introduced into the reactor flow channel contains a gene, the reactor may contain a probe which reacts with the gene. This makes it possible to detect a gene having a base sequence corresponding to the probe in the reactor. The probe may be fluorescently labeled.

DETAILED DESCRIPTION OF THE INVENTION

Figure 1A:
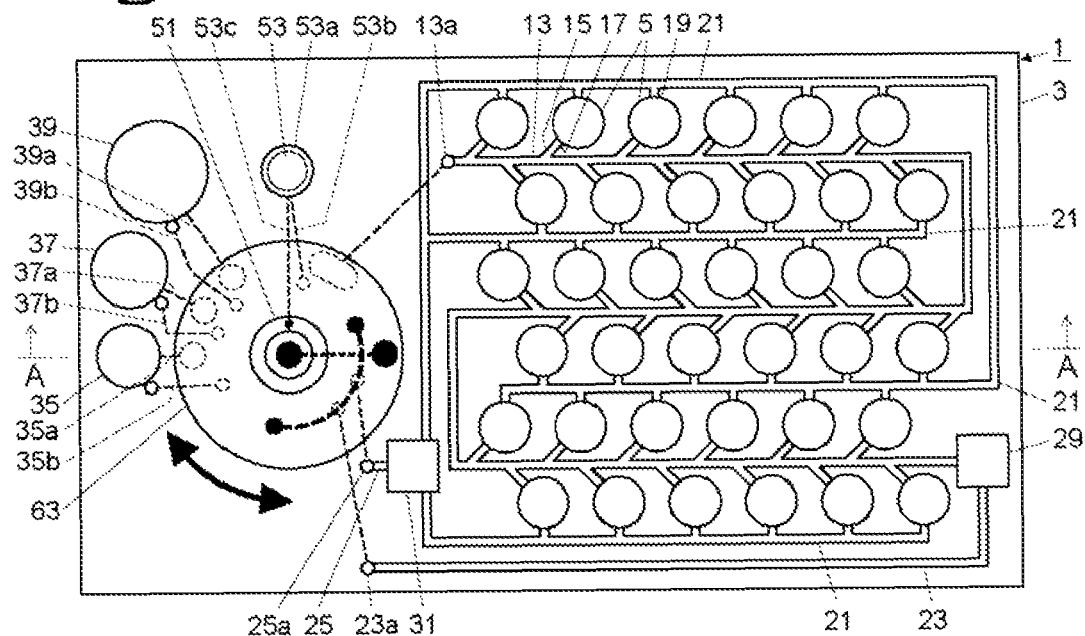
FIG. 1A is a schematic plan view of a reactor plate according to a first embodiment of the present invention.

A reactor plate according to a first embodiment of the present invention will be described with reference to FIGS. 1A to 6F.

A reactor plate 1 includes a container base 3 and a plurality of reactors 5 each having an opening in one surface of the container base 3. According to the first embodiment of the present invention, the reactors 5 are arranged in 6 rows and 6 columns in a zigzag manner. Each of the reactors 5 contains a reagent 7 and a wax 9.

The material of the container base 3 including the reactors 5 is not particularly limited, but is preferably cheaply available when the reactor plate 1 is designed to be disposable. Preferred examples of such a material include resin materials such as polypropylene and polycarbonate. In a case where the reactor plate 1 is designed to be used for detecting a substance in the reactors 5 by absorbance, fluorescence, chemiluminescence or bioluminescence, the container base 3 is preferably made of an optically-transparent resin so that optical detection can be carried out from the bottom surface side thereof. Particularly, in a case where the reactor plate 1 is designed to be used for fluorescence detection, the container base 3 is preferably made of an optically-transparent resin having low self-fluorescence properties (i.e., properties such that the amount of fluorescence emitted from a material itself is low) such as polycarbonate. The thickness of the container base 3 is in the range of 0.2 to 4.0 mm, preferably in the range of 1.0 to 2.0 mm. From the viewpoint of low self-fluorescence properties required for fluorescence detection, the thickness of the container base 3 is preferably small.

Referring to FIGS. 1A to 1C and 3A to 3C, a flow channel base 11 is provided on the container base 3 so as to cover a region where the reactors 5 are arranged. The flow channel base 11 is made of, for example, PDMS (polydimethylsiloxane) or silicone rubber. The thickness of the flow channel base 11 is in the range of, for example, 1.0 to 5.0 mm. The surface of the flow channel base 11 which is in contact with the container base 3 has grooves. The grooves and the surface of the container base 3 form a main flow channel 13, measuring flow channels 15, injection flow channels 17, reactor air drain flow channels 19 and 21, and drain space air drain flow channels 23 and 25. The main flow channel 13, the measuring flow channels 15 and the injection flow channels 17 constitute a reactor flow channel. The surface of the flow channel base 11 which is in contact with the container base 3 also has a plurality of recesses 27 each of which is arranged above the reactor 5. It is to be noted that in FIGS. 1A, 3A, and 3B, the flow channel base 11 itself is not shown, and only the grooves and recesses of the flow channel base 11 are shown.

The main flow channel 13 is constituted from one flow channel, and is bent so as to run in the vicinity of all the reactors 5. One end of the main flow channel 13 is connected to a flow channel 13a constituted from a through hole provided in the container base 3. The flow channel 13a is connected to a port of a switching valve 63 which will be described later. The other end of the main flow channel 13 is connected to a liquid drain space 29 provided in the container base 3. The main flow channel 13 is constituted from a groove having a depth of, for example, 400 µm and a width of, for example, 500 µm. Further, a part of the main flow channel 13 having a predetermined length of, for example, 250 µm and located downstream of a position where the measuring flow channel 15 is connected to the main flow channel 13 is narrower than the other part of the main flow channel 13, and has a width of, for example, 250 µm.

The measuring flow channel 15 branches off from the main flow channel 13, and is provided for each of the reactors 5. The end of the measuring flow channel 15 located on the opposite side from the main flow channel 13 is arranged in the vicinity of the reactor 5. The measuring flow channel 15 is constituted from a groove having a depth of, for example, 400 µm. The measuring flow channel 15 has a predetermined internal capacity of, for example, 2.5 µL. The width of a part of the measuring flow channel 15 connected to the main flow channel 13 is, for example 500 µm, which is larger than that of the above-described narrow-width part of the main flow channel 13. This makes the flow resistance of a liquid coming from one end of the main flow channel 13 larger in the narrow-width part of the main flow channel 13 than in the measuring flow channel 15 branching off from the main flow channel 13. Therefore, a liquid coming from one end of the main flow channel 13 first flows into the measuring flow channel 15 to fill the measuring flow channel 15, and then flows downstream through the narrow-width part of the main flow channel 13.

The injection flow channel 17 is also provided for each of the reactors 5. One end of the injection flow channel 17 is connected to the measuring flow channel 15. The other end of the injection flow channel 17 is connected to the recess 27 located above the reactor 5, and is therefore led to the space above the reactor 5. The injection flow channel 17 is formed to have such a size that the liquid tightness of the reactor 5 is kept without creating a pressure difference between the inside of the reactor 5 and the inside of the injection flow channel 17. According to the first embodiment of the present invention, the injection flow channel 17 is constituted from a plurality of grooves, and each of the grooves has a depth of, for example, 10 µm and a width of, for example 20 µm. More specifically, the injection flow channel 17 is provided in a region having a width of 500 µm, and is constituted from 13 grooves formed at a pitch of 40 µm. Therefore, the area of the interface between each groove constituting the injection flow channel 17 and the measuring flow channel 15, that is, the cross-sectional area of each groove constituting the injection flow channel 17 is 200 µm$^2$. The recess 27 has a depth of, for example, 400 µm, and has a circular cross section smaller than the opening of the reactor 5.

The flow channel 19 is also provided for each of the reactors 5. One end of the flow channel 19 is connected to the recess 27, which is located above the reactor 5, at a position different from the position where the injection flow channel 17 is connected thereto, and is therefore arranged above the reactor 5. The flow channel 19 is formed to have such a size that the liquid tightness of the reactor 5 is kept without creating a pressure difference between the inside of the reactor 5 and the inside of the flow channel 19. The other end of the flow channel 19 is connected to the flow channel 21. According to the first embodiment of the present invention, the flow channel 19 is constituted from a plurality of grooves, and each of the grooves has a depth of, for example, 10 µm and a width of, for example, 20 µm. More specifically, the flow channel 19 is provided in a region having a width of 500 µm, and is constituted from 13 grooves formed at a pitch of 40 µm.

According to the first embodiment of the present invention, the flow channel 21 is constituted from two or more flow channels. To each of the flow channels constituting the flow channel 21, the plurality of flow channels 19 are connected. The flow channel 21 is provided to connect the flow channels 19 to an air drain space 31 provided in the container base 3. The flow channel 21 is constituted from a groove having a depth of, for example, 400 µm and a width of, for example, 500 µm.

The flow channel 23 is provided to connect a liquid drain space 29 to a port of the switching valve 63 which will be described later. One end of the flow channel 23 is located above the liquid drain space 29. The other end of the flow channel 23 is connected to a flow channel 23a constituted from a through hole provided in the container base 3. The flow channel 23a is connected to the port of the switching valve 63 which will be described later. The flow channel 23 is constituted from a groove having a depth of, for example, of 400 μm and a width of, for example 500 μm.

The flow channel 25 is provided to connect the air drain space 31 to a port of the switching valve 63 which will be described later. One end of the flow channel 25 is located above the air drain space 31. The other end of the flow channel 25 is connected to a flow channel 25a constituted from a through hole provided in the container base 3. The flow channel 25a is connected to the port of the switching valve 63 which will be described later. The flow channel 25 is constituted from a groove having a depth of, for example, 400 μm and a width of, for example, 500 μm.

On the flow channel base 11, a flow channel cover 33 (not shown in FIG. 1A) is provided. The flow channel cover 33 is provided to fix the flow channel base 11 onto the container base 3. The flow channel base 33 has a plurality of through holes each of which is arranged above the reactor 5.

Referring to FIGS. 1A to 1C and 4A to 6F, a sample container receiving portion 36, a reagent container receiving portion 38, and an air suction container receiving portion 40 are provided in the container base 3 at positions different from the positions of the reactor 5 arrangement region and the drain spaces 29 and 31. The receiving portion 36 receives a sample container 35, the receiving portion 38 receives a reagent container 37, and the receiving portion 40 receives an air suction container 39. The sample container 35, the reagent container 37 and the air suction container 39 constitute sealed containers of the reactor plate according to the present invention.

As shown in FIGS. 4A to 4F, a sample flow channel 35a and a sample container air drain flow channel 35b are provided in the vicinity of the sample container receiving portion 36 in the container base 3. The sample flow channel 35a is constituted from a through hole extending from the bottom of the receiving portion 36 to the back surface of the container base 3, and the sample container air drain flow channel 35b is constituted from a through hole extending from the top surface to the back surface of the container base 3. The receiving portion 36 has an opening, and around the opening and on the top surface of the container base 3, three locking lugs 35c for holding the sample container 35 are provided.

At the bottom of the receiving portion 36, a projecting flow channel 35d formed so as to project toward the opening of the receiving portion 36 is provided. The proximal end of the projecting flow channel 35d is connected to the sample flow channel 35a. The top surface of the projecting flow channel 35d is beveled against the projection direction of the projecting flow channel 35d.

Further, a second projecting flow channel 35e is provided on the top surface of the container base 3 at a position in the vicinity of the receiving portion 36 so as to project upwardly. The proximal end of the second projecting flow channel 35e is connected to the flow channel 35b. The top surface of the second projecting flow channel 35e is beveled against the projection direction of the second projecting flow channel 35e.

An annular gasket 35f is provided around the proximal end of the projecting flow channel 35d, and another annular gasket 35f is provided around the proximal end of the second projecting flow channel 35e. The gaskets 35f are made of an elastic material such as silicone rubber or PDMS.

The sample container 35 to be received in the receiving portion 36 has a sample container main space 35g, a communicating flow channel 35h, and an air drain space 35i.

A main body of the sample container is made of a resin material such as polypropylene or polycarbonate, and the sample container main space 35g is provided so as to pass through the sample container main body from the upper surface to the lower surface thereof. An opening of the main space 35g provided on the lower surface side thereof is sealed by attaching a film 35j (penetrable portion) made of, for example, aluminum to the lower surface of the sample container main body. Another opening of the main space 35g provided on the upper surface side thereof is sealed by attaching a film 35k made of, for example, aluminum to the upper surface of the sample container main body.

The flow channel 35h is formed by covering a groove provided in the upper surface of the sample container main body with the film 35k, and is located at a position higher than the level of a liquid contained in the sample container. The groove for forming the flow channel 35h is constituted from one or more slits having a width of, for example, 5 to 200 μm and a depth of, for example, 5 to 200 μm. The flow channel 35h is provided to keep the liquid tightness of the main space 35g without creating a pressure difference between the inside of the main space 35g and the inside of the air drain space 35i.

The sample container main body has a projection provided so as to project from the upper lateral surface thereof, and the air drain space 35i is provided in the projection so as to pass through the projection from the upper surface to the lower surface thereof. The inner diameter of the air drain space 35i is, for example, 3 mm or less. According to the first embodiment of the present invention, the inner diameter of the air drain space 35i is 2 mm. An opening of the air drain space 35i provided on the lower surface side thereof is sealed by attaching a film 35l (second penetrable portion) made of, for example, aluminum to the lower surface of the projection. Another opening of the air drain space 35i provided on the upper surface side thereof is sealed with the film 35k.

Figure 4A:
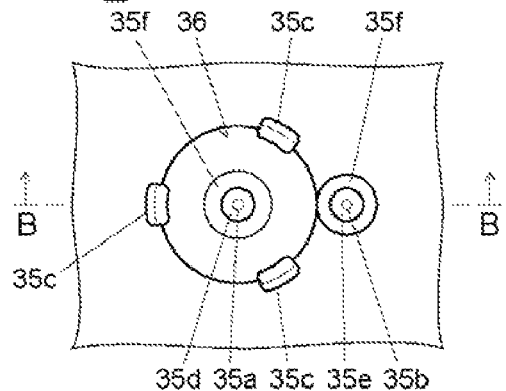
FIG. 4A is a plan view of a sample container receiving portion of the reactor plate according to the first embodiment of the present invention for showing enlarged sectional views of the sample container receiving portion and a sample container.
Figure 4C:
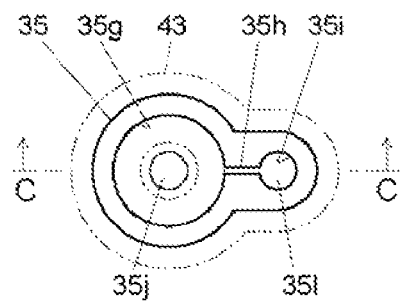
FIG. 4C is a plan view of the sample container.
Figure 4B:
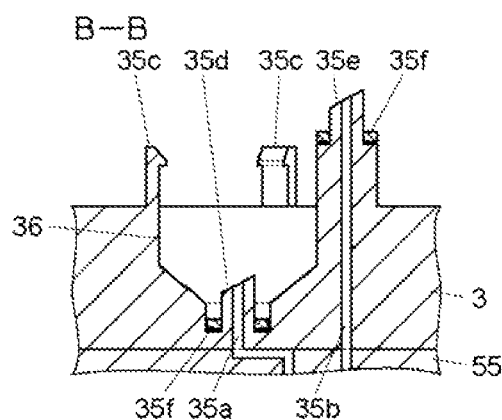
FIG. 4B is a sectional view taken along the B-B line in FIG. 4A.
Figure 4D:
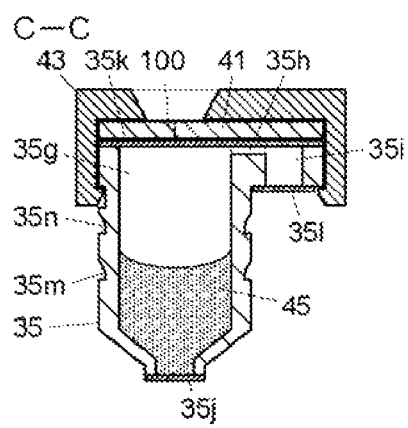
FIG. 4D is a sectional view taken along the C-C line in FIG. 4C.
Figure 4E:
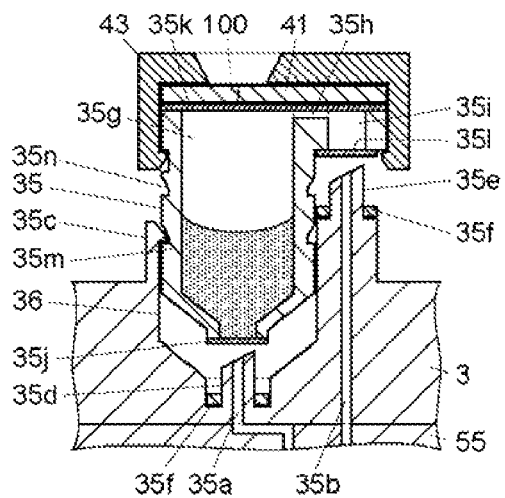
FIG. 4E is a sectional view showing the sample container held at a first holding position in the sample container receiving portion.
Figure 4F:
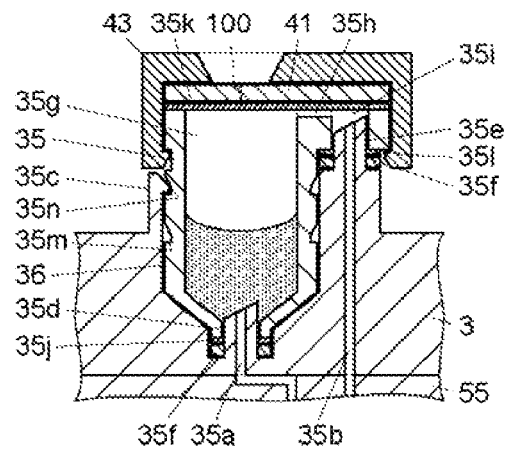
FIG. 4F is a sectional view showing the sample container held at a second holding position in the sample container receiving portion.
Figure 5A:
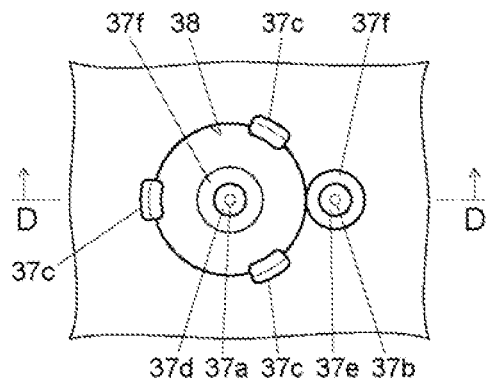
FIG. 5A is a plan view of a reagent container receiving portion of the reactor plate according to the first embodiment of the present invention for showing enlarged sectional views of the reagent container receiving portion and a reagent container.
Figure 5C:
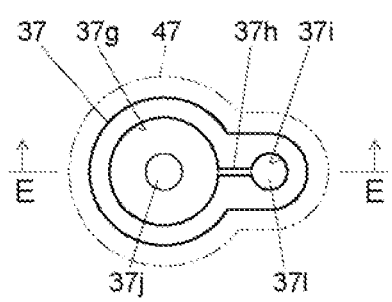
FIG. 5C is a plan view of the reagent container.
Figure 5B:
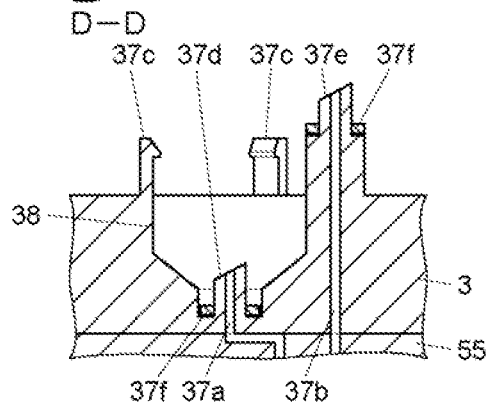
FIG. 5B is a sectional view taken along the D-D line in FIG. 5A.
Figure 5D:
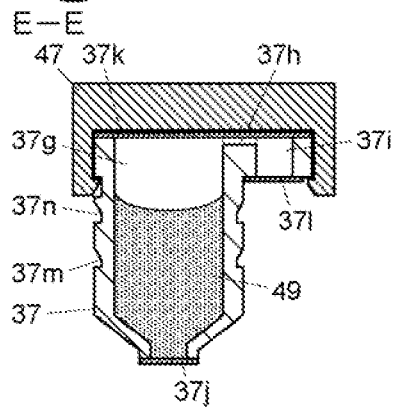
FIG. 5D is a sectional view taken along the E-E line in FIG. 5C.
Figure 5E:
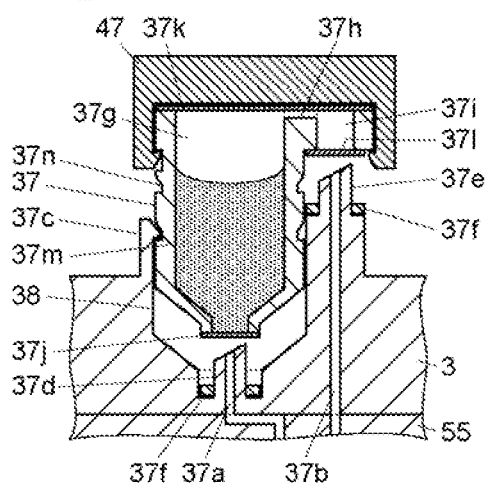
FIG. 5E is a sectional view showing the reagent container held at a first holding position in the reagent container receiving portion.
Figure 5F:
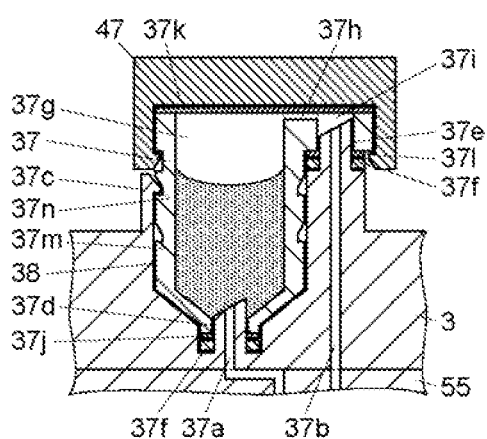
FIG. 5F is a sectional view showing the reagent container held at a second holding position in the reagent container receiving portion.
Figure 6A:
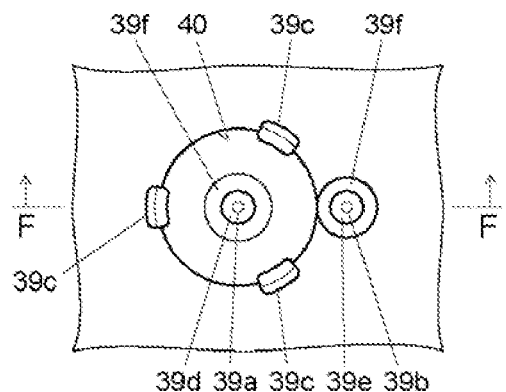
FIG. 6A is a plan view of an air suction container receiving portion of the reactor plate according to the first embodiment of the present invention for showing enlarged sectional views of the air suction container receiving portion and an air suction container.
Figure 6C:
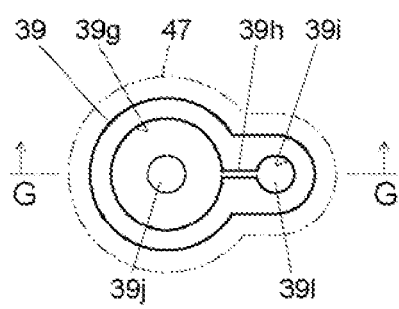
FIG. 6C is a plan view of the air suction container.
Figure 6B:
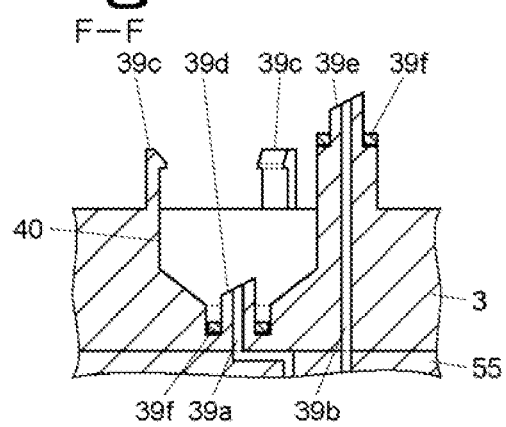
FIG. 6B is a sectional view taken along the F-F line in FIG. 6A.
Figure 6D:
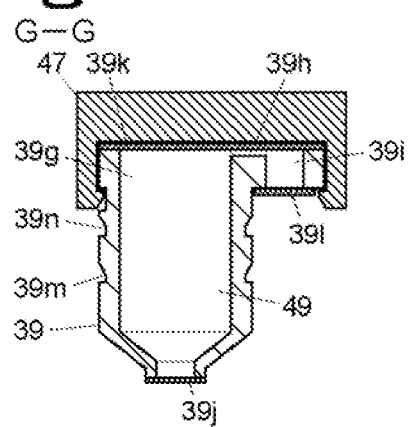
FIG. 6D is a sectional view taken along the G-G line in FIG. 6C.
Figure 6E:
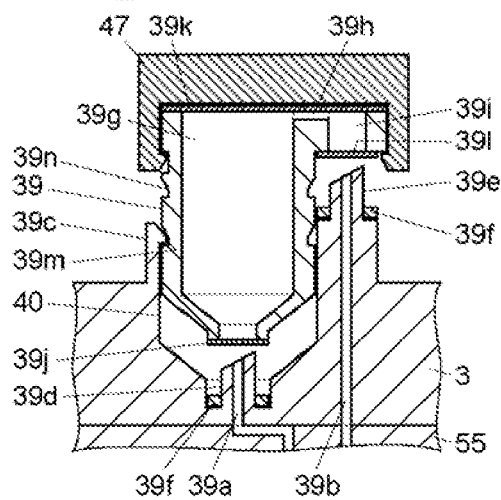
FIG. 6E is a sectional view showing the air suction container held at a first holding position in the air suction container receiving portion.
Figure 6F:
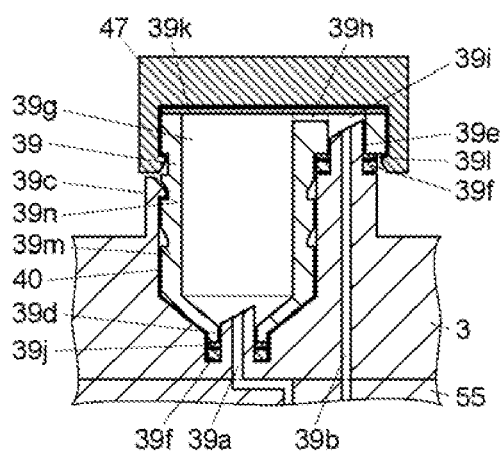
FIG. 6F is a sectional view showing the air suction container held at a second holding position in the air suction container receiving portion.

On the film 35k, a septum 41 as an elastic member is provided. The septum 41 is made of an elastic material such as silicone rubber or PDMS, and therefore, a dispensing tool having a sharp tip can penetrate through the septum 41 to form a through hole closable by pulling out the dispensing tool due to its elasticity. On the septum 41, a septum stopper 43 for fixing the septum 41 is further provided. The septum stopper 43 has an opening arranged above the sample container 35. According to the first embodiment of the present invention, a reagent 45 is previously contained in the main space 35g. In FIGS. 4D to 4F, the septum stopper 43 is fixed to the sample container main body by a locking lug of the septum stopper 43. In this regard, it is to be noted that the number of the locking lugs of the septum stopper 43 is not particularly limited. Further, a method for fixing the septum stopper 43 to the sample container main body is not particularly limited. For example, the septum stopper 43 may be fixed to the sample container main body using an adhesive.

The septum 41 may have a cut 100 passing through the center of the main space 35g when seen from above. In a case where the septum 41 is circular when seen from above, the cut 100 is preferably of a single straight line type extending in the diameter direction of the septum 41 or a cross-shaped type having an intersection at the center of the septum 41. As described above, since the septum 41 is made of an elastic material, the cut 100 is opened by inserting a sample dispensing tool into the septum 41 and is closed by pulling out the sample dispensing tool due to its elasticity so that the sample container 35 is hermetically sealed again.

The lateral surface of the sample container main body has locking grooves 35m and 35n. The locking grooves 35m and 35n are provided so that the sample container 35 can be held by the locking lugs 35c at a first holding position or a second holding position in the sample container receiving portion 36.

The locking groove 35m is provided lower than the locking groove 35n to hold the sample container 35 at the first holding position (see FIG. 4E). The locking groove 35n is provided to hold the sample container 35 at the second holding position (see FIG. 4F). The locking lugs 35c and the locking grooves 35m and 35n constitute a sealed container holding system of the reactor plate according to the present invention. However, the sealed container holding system is not limited to one constituted from the locking lugs 35c and the locking grooves 35m and 35n, and can have any structure as long as it can hold the sample container 35 (sealed container) at the first holding position and the second holding position.

As shown in FIG. 4E, at the first holding position, the film 35j and the projecting flow channel 35d are opposed to each other, and the film 35l and the second projecting flow channel 35e are also opposed to each other. The sample container 35 can be shifted from the first holding position to the second holding position by pushing the sample container 35 toward the container base 3.

By pushing the sample container 35 toward the container base 3, the tip of the projecting flow channel 35d is allowed to penetrate through the film 35j into the main space 35d and the tip of the second projecting flow channel 35e is also allowed to penetrate through the film 35l into the air drain space 35i. As shown in FIG. 4F, at the second holding position, the main space 35g is connected to the sample container flow channel 35a through the projecting flow channel 35d, and the air drain space 35i is connected to the flow channel 35b through the projecting flow channel 35e. At the second holding position, the lower surface of the sample container main body of the sample container 35 is being pressed against the gaskets 35f. This makes it possible to establish highly airtight connections between the main space 35g and the flow channel 35a and between the air drain space 35i and the flow channel 35b, thereby preventing liquid leakage and air leakage. However, a method for preventing liquid leakage and air leakage is not limited to providing the gaskets 35f, and any method can be employed as long as the sample container 35 can be airtightly connected to the flow channels 35a and 35b.

By holding the sample container 35 at the first holding position, it is possible to store the reactor plate with the sample container 35 and the flow channel 35a being separated from each other. Therefore, even when the main space 35g contains a liquid such as the reagent 45 or dilution water or a powdered solid such as a reagent during storage of the reactor plate, the liquid or solid does not flow into the flow channel 35a.

Further, at the first holding position, the main space 35g and the air drain space 35i are in a hermetically-sealed state, and therefore a liquid such as the reagent 45 or dilution water is prevented from being evaporated even when it is previously contained in the main space 35g.

Hereinbelow, the reagent container 37 and the reagent container receiving portion 38 will be described with reference to FIGS. 5A to 5F.

The reagent container receiving portion 38 has the same structure as the sample container receiving portion 36 described above with reference to FIGS. 4A to 4F. More specifically, the reagent container receiving portion 38 has a reagent flow channel 37a, a reagent container air drain flow channel 37b, locking lugs 37c, a projecting flow channel 37d, a second projecting flow channel 37e and gaskets 37f.

The reagent container 37 has the same structure as the sample container 35 described above with reference to FIGS. 4A to 4F except that it does not have a septum 41 but has a cover 47 instead of a septum stopper 43. That is, the reagent container 37 has a reagent container main space 37g, a communicating flow channel 37h, a reagent container air drain space 37i, films 37j, 37k, and 37l, locking grooves 37m and 37n, and the cover 47. The cover 47 is provided to prevent the breakage of the film 37k attached to the upper surface of a main body of the reagent container 37. The reagent container main space 37g contains dilution water 49. It is to be noted that the cover 47 is fixed to the reagent container main body by a locking lug of the cover 47, but the number of the locking lugs of the cover 47 is not particularly limited. Further, a method for fixing the cover 47 to the reagent container main body is not particularly limited. For example, the cover 47 may be fixed to the reagent container main body using an adhesive.

As in the case of the sample container 35, the reagent container 37 is held at a first holding position (see FIG. 5E) and a second holding position (see FIG. 5F) in the reagent container receiving portion 38. The reagent container 37 is connected to the reagent container flow channel 37a and the air drain flow channel 37b in the same manner as in the case of the connection of the sample container 35 to the flow channel 35a and the air drain flow channel 35b described above with reference to FIGS. 4A to 4F.

By holding the reagent container 37 at the first holding position, it is possible to store the reactor plate with the reagent container 37 and the reagent container flow channel 37a being separated from each other. Therefore, even when the reagent container main space 37g contains a liquid such as a reagent or the dilution water 49, or a powdered solid such as a reagent during storage of the reactor plate, the liquid or solid does not flow into the reagent container flow channel 37a.

Further, at the first holding position, the reagent container main space 37g and the air drain space 37i are in a hermetically-sealed state, and therefore, a liquid such as a reagent or the dilution water 49 is prevented from being evaporated even when it is previously contained in the reagent container main space 37g.

Hereinbelow, the air suction container 39 and the air suction container receiving portion 40 will be described with reference to FIGS. 6A to 6F.

The air suction container receiving portion 40 has the same structure as the reagent container receiving portion 38 described above with reference to FIGS. 5A to 5F. More specifically, the air suction container receiving portion 40 has an air suction flow channel 39a, an air suction container air drain flow channel 39b, locking lugs 39c, a projecting flow channel 39d, a second projecting flow channel 39e, and gaskets 39f.

The air suction container 39 has the same structure as the reagent container 37 described above with reference to FIGS. 5A to 5F. More specifically, the air suction container 39 has an air suction container main space 39g, a communicating flow channel 39h, an air suction container air drain space 39i, films 39j, 39k, and 39l, locking grooves 39m and 39n, and a cover 47. The air suction container main space 39g contains neither a liquid nor a solid, but is filled with air.

As in the cases of the sample container 35 and the reagent container 37, the air suction container 39 is held at a first holding position (see FIG. 6E) and a second holding position (see FIG. 6F) in the air suction container receiving portion 40. The air suction container 39 is connected to the air suction container flow channel 39a and the air suction container air drain flow channel 39b in the same manner as in the case of the connection of the sample container 35 to the flow channel 35a and the air drain flow channel 35b described above with reference to FIGS. 4A to 4F.

Figure 1B:
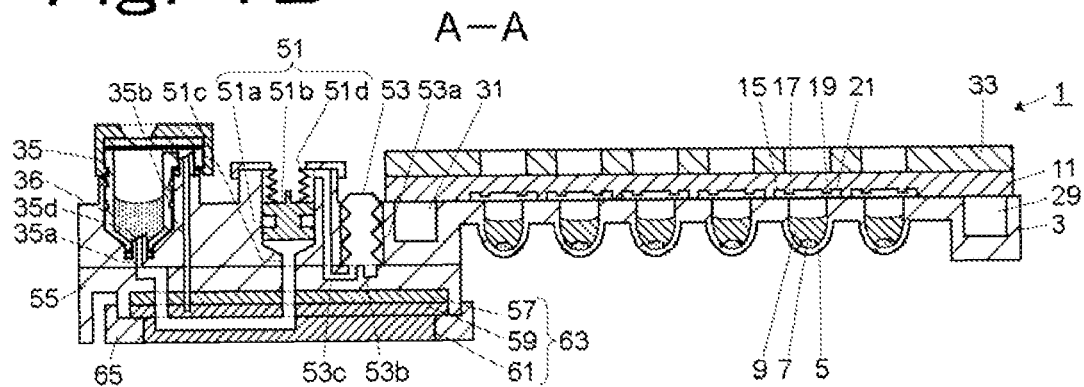
FIG. 1B is a schematic sectional view taken along the A-A line in FIG. 1A and further showing a bellows, drain spaces, measuring flow channels, injection flow channels and sample container air drain flow channel.
Figure 1C:
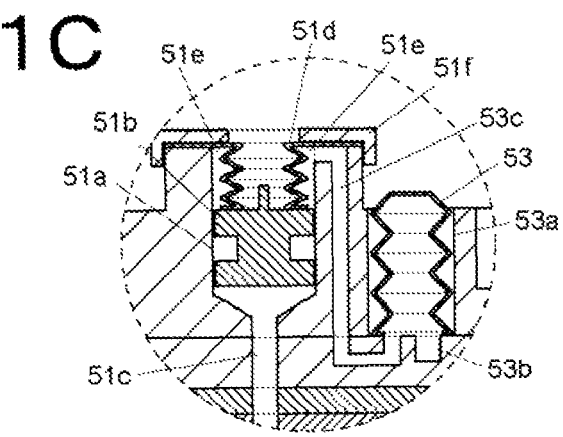
FIG. 1C is a partially-enlarged sectional view schematically showing a syringe, the bellows and their vicinity.
Figure 2:
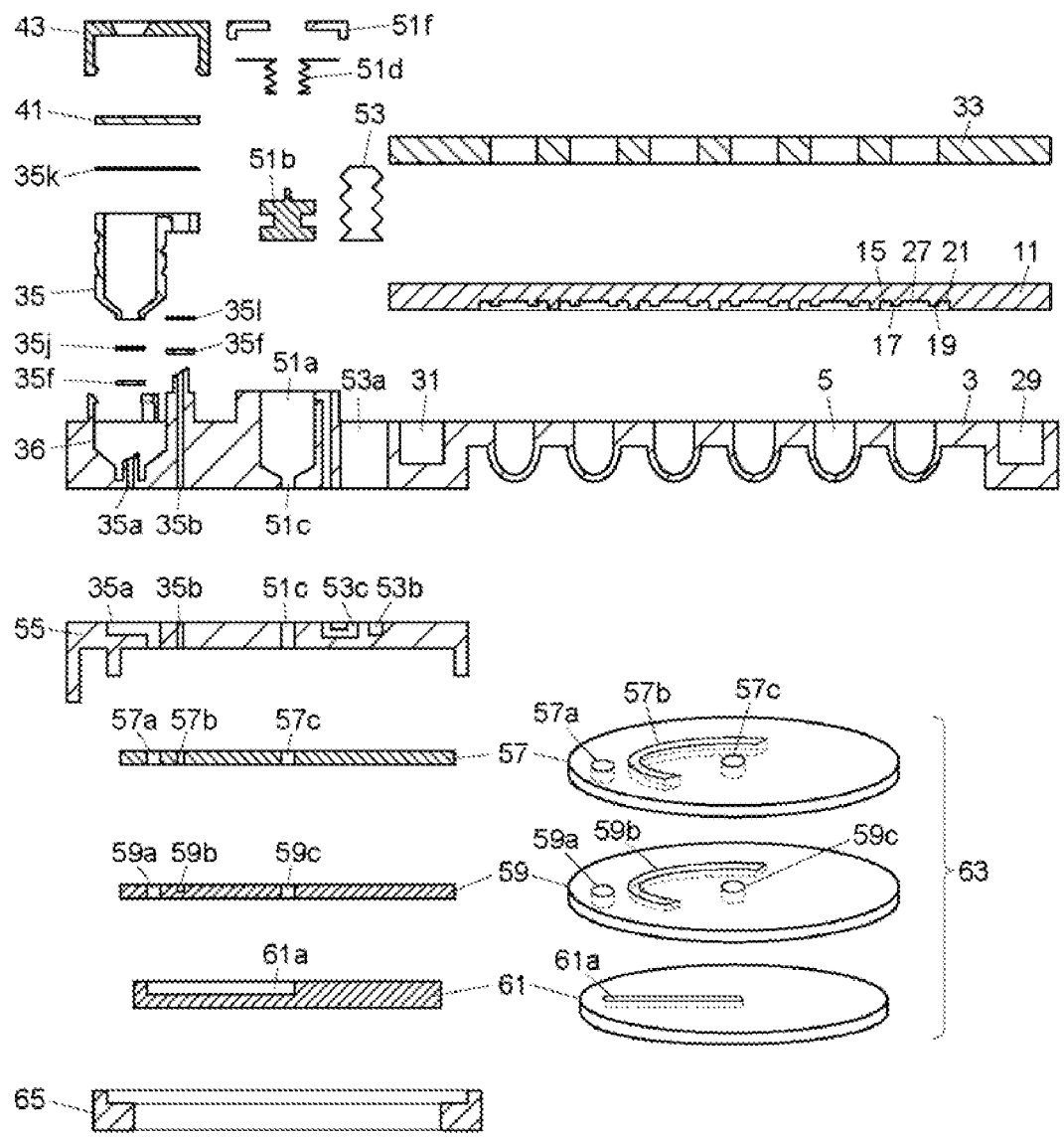
FIG. 2 shows an exploded sectional view of the reactor plate according to the first embodiment of the present invention and a schematic exploded perspective view of a switching valve.
Figure 3A:
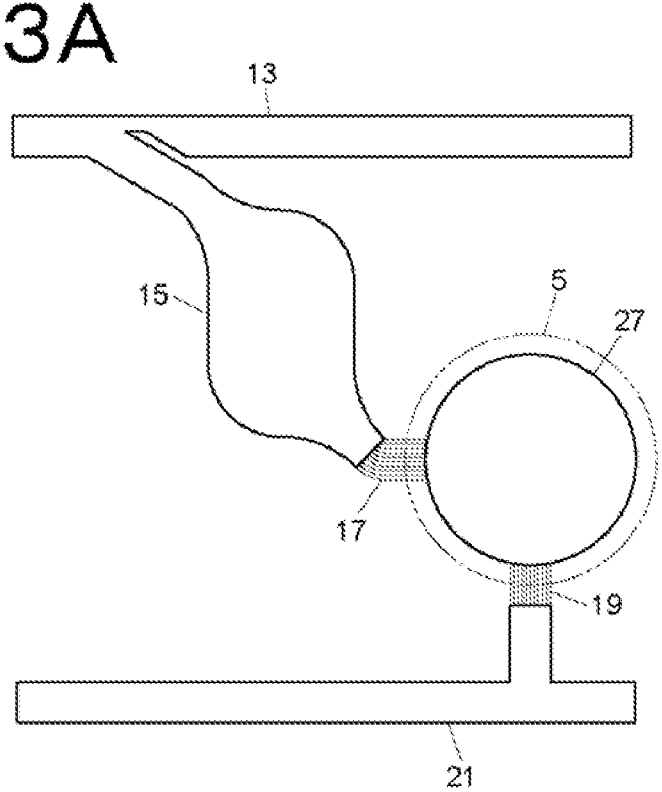
FIGS. 3A to 3C are a schematic plan view, a perspective view, and a sectional view of one reactor and its vicinity of the reactor plate according to the first embodiment of the present invention, respectively.
Figure 3B:
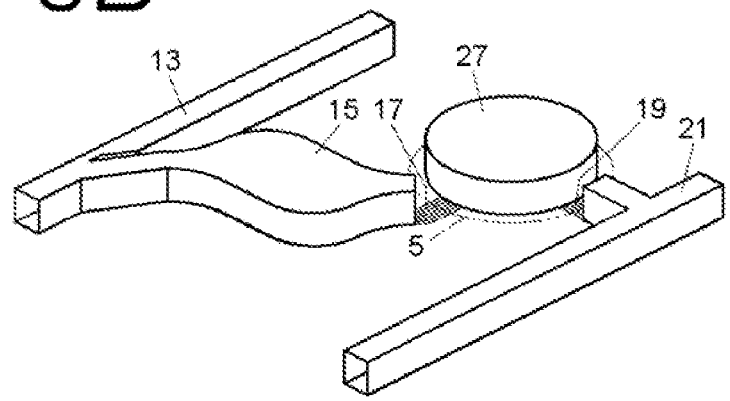
Figure 3C:
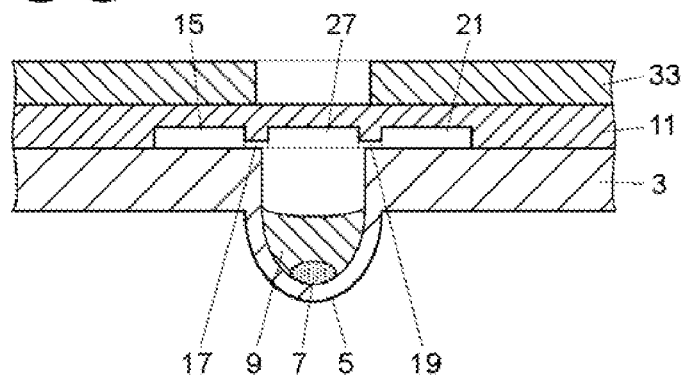

Referring to FIGS. 1A to 1C and FIG. 2 again, a syringe 51 is provided on the surface of the container base 3 at a position different from the positions of the reactor 5 arrangement region, the drain spaces 29 and 31, and the container receiving portions 36, 38 and 40. The syringe 51 is constituted from a cylinder 51a provided in the container base 3, a plunger 51b arranged in the cylinder 51a, and a cover body 51d. Further, the cylinder 51a has a discharge port at the bottom thereof, and a syringe flow channel 51c constituted from a through hole extending from the discharge port to the back surface of the container base 3 is provided in the container base 3.

The cover body 51d has flexibility in the sliding direction of the plunger 51b and is connected to the cylinder 51a and the plunger 51b. The cover body 51d is provided to create a sealed space 51e to cut off the inner wall of the cylinder 51a to be brought into contact with the plunger 51b from an atmosphere outside the cylinder 51a. The sealed space 51e is a space enclosed with the cylinder 51a, the plunger 51b and the cover body 51d. The end of the cover body 51d connected to the cylinder 51a is fixed to the upper end of the cylinder 51a by a cylinder cap 51f so that the airtightness of the sealed space 51e can be ensured. On the other hand, the other end of the cover body 51d is connected to the upper surface of the plunger 51b using an adhesive so that the airtightness of the sealed space 51e can be ensured. However, a method for connecting the cover body 51d to the cylinder 51a and the plunger 51b is not limited to the method described above, and the connecting positions of the cover body 51d are not limited to those described above.

As described above, since the cover body 51d is connected to the cylinder 51a and the plunger 51b to create a sealed space 51e enclosed with them, the entry of foreign matter from the outside and the leakage of a liquid to the outside through a gap between the cylinder 51a and the plunger 51b do not occur, thereby preventing the pollution of an environment outside the reactor plate. It is to be noted that as described above, since the cover body 51d has flexibility in the sliding direction of the plunger 51b, the plunger 51b can be slidably operated.

According to the first embodiment of the present invention, the plunger 51b and the cover body 51d are provided as separate members but may be integrally molded. The plunger and the cover body can be integrally molded using, for example, silicone rubber.

The container base 3 also has a bellows 53 provided at a position different from the positions of the reactor 5 arrangement region, the drain spaces 20 and 31, the containers 35, 37 and 39, and the syringe 51. The internal space of the bellows 53 is sealed, and the internal volume of the bellows 53 is passively variable by expansion and contraction. The bellows 53 is arranged in, for example, a through hole 53a provided in the container base 3.

A container bottom 55 is attached to the back surface of the container base 3 at a position different from the position of the reactor 5 arrangement region. The container bottom 55 has an air drain flow channel 53b provided at such a position that the air drain flow channel 53b can communicate with the bellows 53. The bellows 53 is in close contact with and is connected to the surface of the container bottom 55. The container bottom 55 is provided to lead the flow channels 13a, 23a, 25a, 35a, 35b, 37a, 37b, 39a, 39b, 51c and 53b to predetermined port positions.

In the container base 3 and the container bottom 55, a syringe air drain flow channel 53c is provided whose one end is connected to the sealed space 51e and other end is connected to the inside of the bellows 53. It is to be noted that, in FIG. 1A, the syringe air drain flow channel 53c is not shown.

By providing such a syringe air drain flow channel 53c whose one end is connected to the sealed space 51e and other end is connected to the inside of the bellows 53, it is possible to relieve a pressure change in the sealed space 51e caused by a change in the internal capacity of the sealed space 51e during the sliding of the plunger 51b while the sealed space 51e is cut off from an atmosphere outside the reactor plate 1. This makes it possible to smoothly slide the plunger 51b.

On the surface of the container bottom 55 located on the opposite side from the container base 3, a rotary switching valve 63 constituted from a disk-shaped sealing plate 57, rotor upper plate 59, and rotor base 61 is provided. The switching valve 63 is attached to the container bottom 55 by means of a lock 65.

The sealing plate 57 has a through hole 57a provided in the vicinity of the peripheral portion thereof, a through groove 57b provided on a concentric circle thereof closer to the center thereof than the through hole 57a, and a through hole 57c provided at the center thereof. The through hole 57a is to be connected to any one of the flow channels 13a, 35a, 37a, and 39a, the through groove 57b is to be connected to at least two of the flow channels 23a, 25a, 35b, 37b, 39b and 53b, and the through hole 57c is to be connected to the syringe flow channel 51c.

The rotor upper plate 59 has a through hole 59a provided at a position corresponding to the through hole 57a of the sealing plate 57, a groove 59b provided in the surface thereof so as to correspond to the through groove 57b of the sealing plate 57, and a through hole 59c provided at the center thereof.

The rotor base 61 has a groove 61a provided in the surface thereof. The groove 61a connects together the two through holes 59a and 59c provided at the peripheral portion and center of the rotor upper plate 59, respectively.

By rotating the switching valve 63, it is possible to connect the syringe flow channel 51c to any one of the flow channels 13a, 35a, 37a and 39a, and at the same time to connect the air drain flow channel 53b to at least any one of the flow channels 23a, 25a, 35b, 37b and 39b.

The switching valve 63 shown in FIG. 1A is in its initial state, and therefore the syringe flow channel 51c is not connected to any of the flow channels 13a, 35a, 37a and 39a, and the air drain flow channel 53b is not connected to any of the flow channels 23a, 25a, 35b, 37b and 39b either.

In the reactor plate 1, the injection flow channel 17 is formed so that the liquid tightness of the reactor 5 can be kept without creating a pressure difference between the inside of the reactor 5 and the inside of the injection flow channel 17. The flow channel 19 is also formed so that the liquid tightness of the reactor 5 can be kept without creating a pressure difference between the inside of the reactor 5 and the inside of the flow channel 19. The main flow channel 13 of the reactor flow channel, the liquid drain space 29 connected to the main flow channel 13 and the flow channel 23 can be hermetically sealed by operating the switching valve 63. The containers 35, 37 and 39 are sealed with the septum 41 or the cover 47. The flow channels 35a, 35b, 37a, 37b, 39a and 39b connected to the containers 35, 37 and 39 can be hermetically sealed by operating the switching valve 63. One end of the air drain flow channel 53b is hermetically sealed by being connected to the bellows 53. In this way, the containers and the flow channels provided in the reactor plate 1 constitute a closed system. It is to be noted that even when the reactor plate 1 does not have a bellows 53, or the air drain flow channel 53b is in communication with an atmosphere outside the reactor plate 1, the air drain flow channel 53b can be cut off from the containers and the flow channels other than the air drain flow channel 53b provided in the reactor plate 1 by operating the switching valve 63, and therefore the containers for containing a liquid and the flow channels for allowing a liquid to flow can be hermetically sealed.

Figure 7:
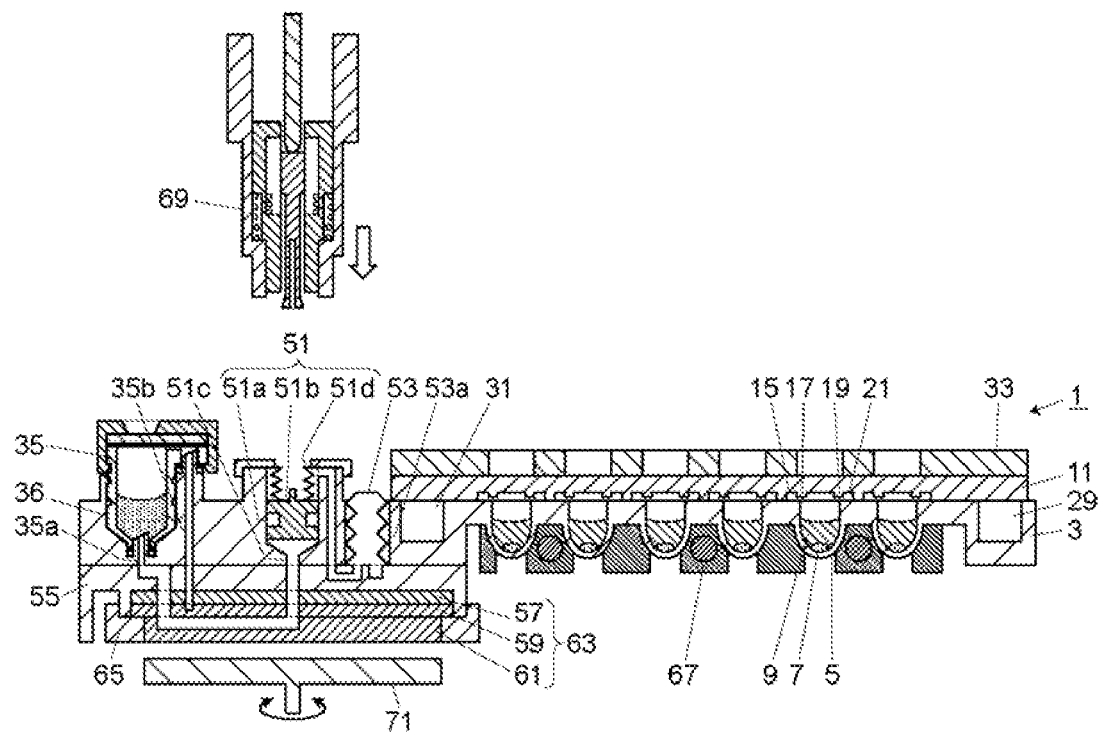
FIG. 7 is a sectional view schematically showing a reaction treatment device for treating the reactor plate and the reactor plate.

FIG. 7 is a sectional view showing a reaction treatment device for treating the reactor plate 1 shown in FIGS. 1A to 1C and the reactor plate 1. The reactor plate 1 shown in FIG. 7 has the same structure as the reactor plate 1 shown in FIGS. 1A to 1C, and therefore, the explanation thereof will be omitted.

The reaction treatment device includes a temperature control system 67 for controlling the temperature of the reactors 5, a syringe driving unit 69 for driving the syringe 51, and a switching valve driving unit 71 for operating the switching valve 63.

FIGS. 8 to 14 are plan views for explaining the operation of introducing a sample liquid from the sample container 35 into the reactors 5. The operation will be described with reference to FIGS. 1A to 1C and FIGS. 8 to 14.

The sample container 35, the reagent container 37 and the air suction container 39 are held at the first holding position, and in this state, a sharp-tipped dispensing tool (not shown) is allowed to penetrate through the septum 41 provided on the sample container 35 to dispense, for example, 5 µL of a sample liquid into the sample container 35. After the completion of dispensing the sample liquid, the dispensing tool is pulled out of the septum 41. A through hole formed in the septum 41 by the dispensing tool is closed by pulling the dispensing tool out of the septum 41 due to its elasticity.

In a case where the septum 41 has a cut 100, a pressure in the sample container 35 is not increased even by inserting a sample dispensing tool into the sample container 35. This makes it possible to easily dispense a trace amount of sample liquid.

The sample container 35, the reagent container 37 and the air suction container 39 held at the first holding position are pushed toward the container base 3 to shift them to the second holding position. By doing so, it is possible to establish air-tight connections between the main space 35g and the flow channel 35a, between the air drain space 35i and the flow channel 35b, between the reagent container main space 37g and the reagent container flow channel 37a, between the air drain space 37i and the air drain flow channel 37b, between the air suction container main space 39g and the air suction container flow channel 39a, and between the air suction container air drain space 39i and the air suction container air drain flow channel 39b. In this regard, it is to be noted that the sample liquid may be dispensed into the sample container 35 after the sample container 35, the reagent container 37 and the air suction container 39 are shifted to the second holding position by pushing them toward the container base 3.

The syringe driving unit 69 is connected to the plunger 51b of the syringe 51, and the switching valve driving unit 71 is connected to the switching valve 63.

Figure 8:
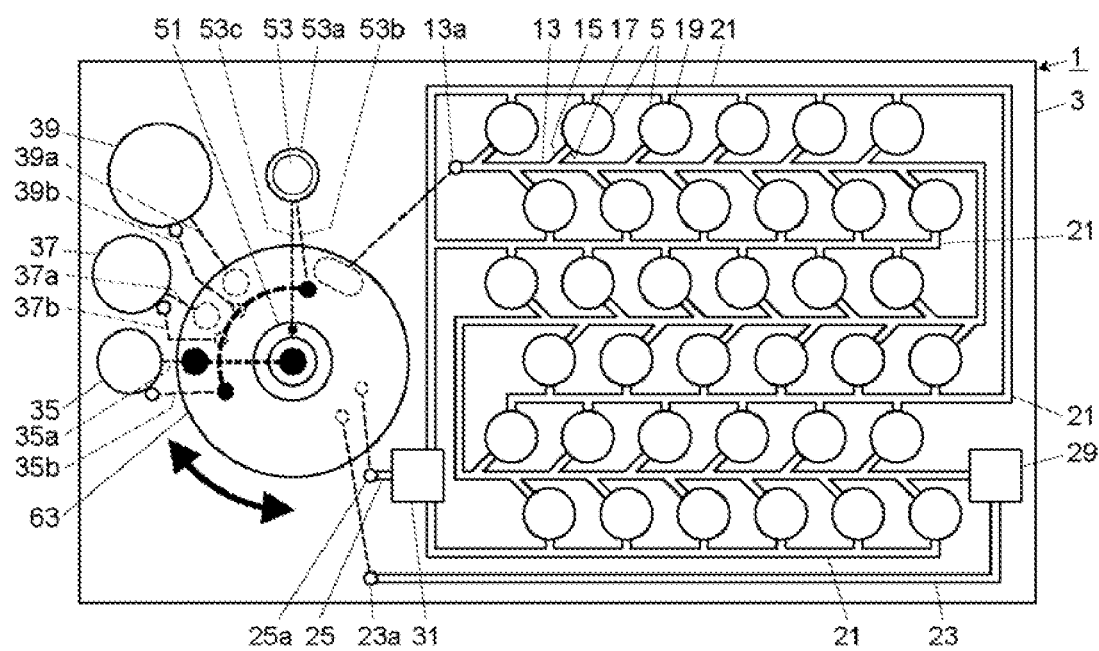
FIG. 8 is a plan view for explaining the operation of introducing a sample liquid from the sample container into the reactors.

As shown in FIG. 8, the switching valve 63 in its initial state shown in FIG. 1A is rotated to connect the sample flow channel 35a to the syringe flow channel 51c and to connect the flow channel 35b to the air drain flow channel 53b. At this time, the air drain flow channels 37b and 39b are also connected to the air drain flow channel 53b. The sample container 35 contains, for example, 45 µL of a sample mixture (i.e., a mixture of a sample and a reagent).

The plunger 51b of the syringe 51 is allowed to slide to mix the sample and reagent contained in the sample container 35. Then, for example, only 10 µL of the sample mixture is sucked from the sample container 35 into the flow channel of the switching valve 63, the syringe flow channel 51c, and the syringe 51. At this time, since the sample container 35 is in communication with the bellows 53 through the air drain flow channels 35e, 35d and 35b, the switching valve 63 and the air drain flow channel 53b, the bellows 53 expands or contracts due to a change in the volume of a gas contained in the sample container 35. Further, the internal volume of the sealed space 51e (see FIG. 1C) is changed due to the deformation of the cover body 51d caused by sliding the plunger 51b. Since the sealed space 51e is in communication with the bellows 53 through the syringe air drain flow channel 53c, the bellows 53 expands or contracts also due to a change in the internal volume of the sealed space 51e. Also in the operation steps described below, the bellow 53 expands or contracts due to a change in the internal volume of the sealed space 51e caused by sliding the plunger 51b.

Figure 9:
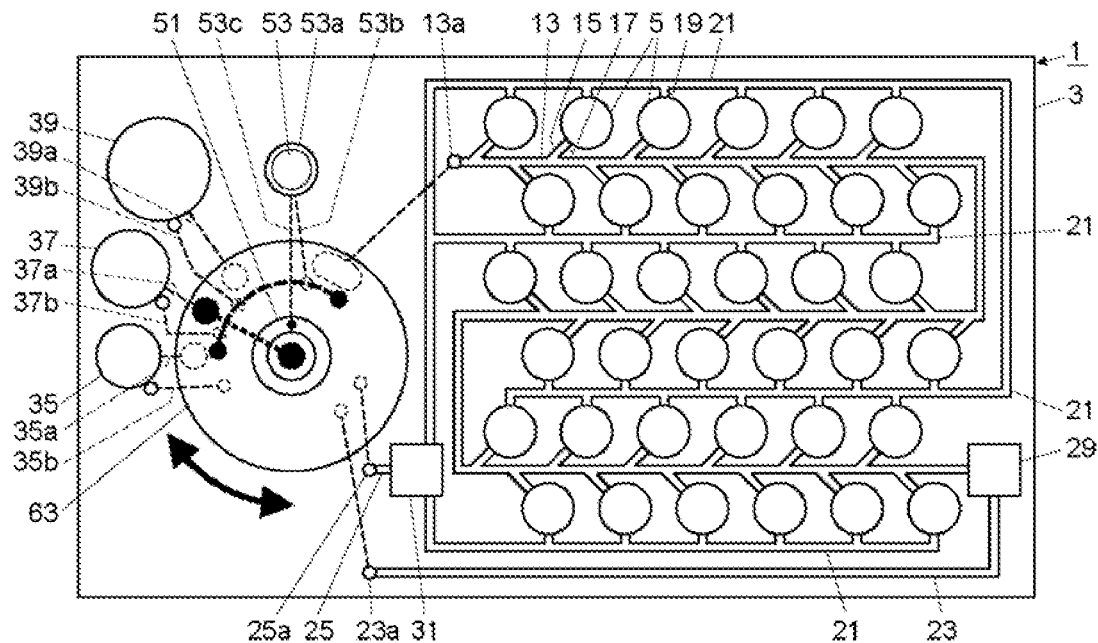
FIG. 9 is a plan view for explaining operation carried out subsequently to the operation shown in FIG. 8.

As shown in FIG. 9, the switching valve 63 is rotated to connect the reagent flow channel 37a to the syringe flow channel 51c and to connect the air drain flow channel 37b to the air drain flow channel 53b. The reagent container 37 previously contains, for example, 190 µL of dilution water 49. The sample mixture, which has been sucked into the flow channel of the switching valve 63, the syringe flow channel 51c and the syringe 51, is injected into the reagent container 37, and then the syringe 51 is allowed to slide to mix the sample mixture and the dilution water 49. Then, for example, the entire amount (i.e., 200 µL) of the diluted sample mixture is sucked into the flow channel of the switching valve 63, the syringe flow channel 51c, and the syringe 51. At this time, since the reagent container 37 is in communication with the bellows 53 through the air drain flow channels 37e, 37d and 37b, the switching valve 63 and the air drain flow channel 53b, the bellows 53 expands or contracts due to a change in the volume of a gas contained in the reagent container 37.

Figure 10:
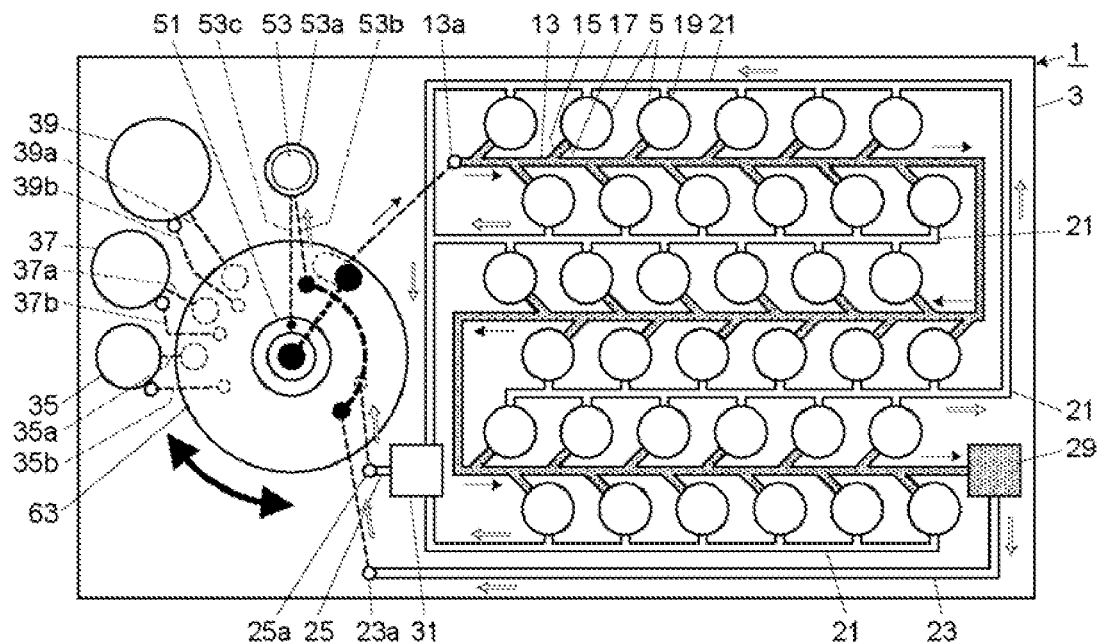
FIG. 10 is a plan view for explaining operation carried out subsequently to the operation shown in FIG. 9.

As shown in FIG. 10, the switching valve 63 is rotated to connect the flow channel 13a, which is connected to one end of the main flow channel 13, to the syringe flow channel 51c and to connect the flow channels 23a and 25a, which are connected to the liquid drain space 29 and the air drain space 31 respectively, to the air drain flow channel 53b. The syringe 51 is operated in its discharge direction to feed the diluted sample mixture, which has been sucked into the flow channel of the switching valve 63, the syringe flow channel 51c and the syringe 51, into the main flow channel 13. As indicated by fine dots and arrows in FIG. 10, the diluted sample mixture injected into the main flow channel 13 through the flow channel 13a fills the measuring flow channels 15 in the order of distance from the flow channel 13a and reaches the liquid drain space 29. Under the liquid introduction pressure at which the diluted sample mixture is introduced into the main flow channel 13 and the measuring flow channels 15, the injection flow channel 17 allows a gas to pass through it but does not allow the diluted sample mixture to pass through it. When the diluted sample mixture is introduced into the measuring flow channel 15 to fill the measuring flow channel 15, a gas contained in the measuring flow channel 15 is transferred into the reactor 5 through the injection flow channel 17. Due to the transfer of the gas from the measuring flow channel 15 into the reactor 5, part of a gas contained in the reactor 5 is transferred into the flow channels 19 and 21. Further, a gas contained in the flow channels between the flow channels 19 and the bellows 53 is sequentially transferred toward the bellows 53 (see open arrows in FIG. 10). When the diluted sample mixture is introduced into the liquid drain space 29, the gas contained in the flow channels between the liquid drain space 29 and the bellows 53 is sequentially transferred toward the bellows 53 (see open arrows in FIG. 10). As a result, the bellows 53 expands.

Figure 11:
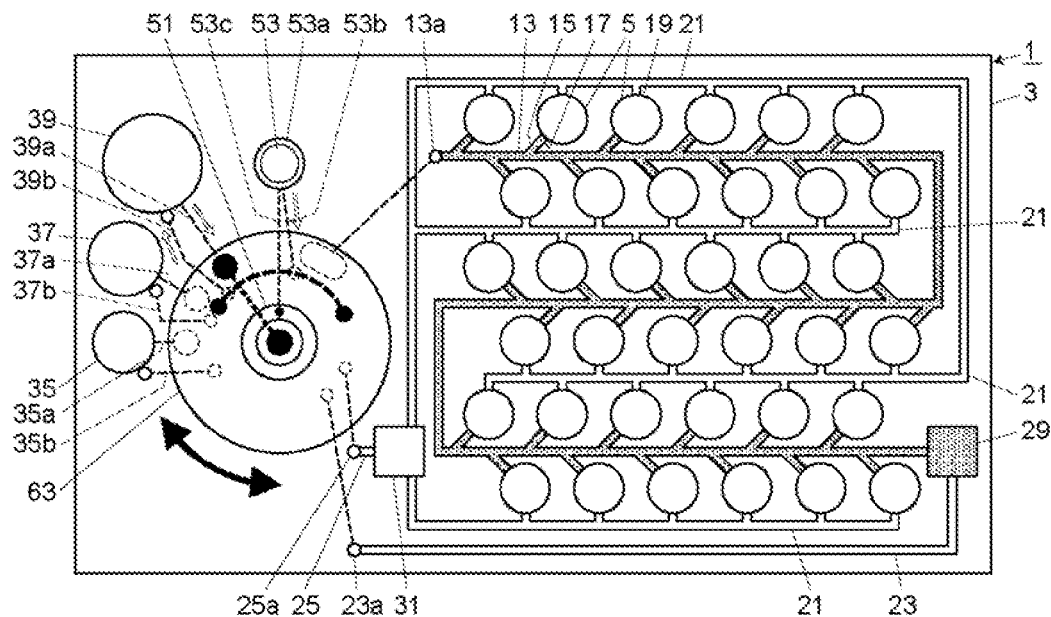
FIG. 11 is a plan view for explaining operation carried out subsequently to the operation shown in FIG. 10.

As shown in FIG. 11, the switching valve 63 is rotated to connect the air suction flow channel 39a to the syringe flow channel 51c and to connect the air suction container air drain flow channel 39b to the air drain flow channel 53b. The syringe 51 is operated in its suction direction to suck a gas from the air suction container 39 into the flow channel of the switching valve 63, the syringe flow channel 51c, and the syringe 51. At this time, since the air suction container 39 is in communication with the bellows 53 through the air drain flow channels 39e, 39d and 39b, the switching valve 63 and the air drain flow channel 53b, the bellows 53 contracts due to a reduction in pressure in the air suction container 39 (see open arrows in FIG. 11).

Figure 12:
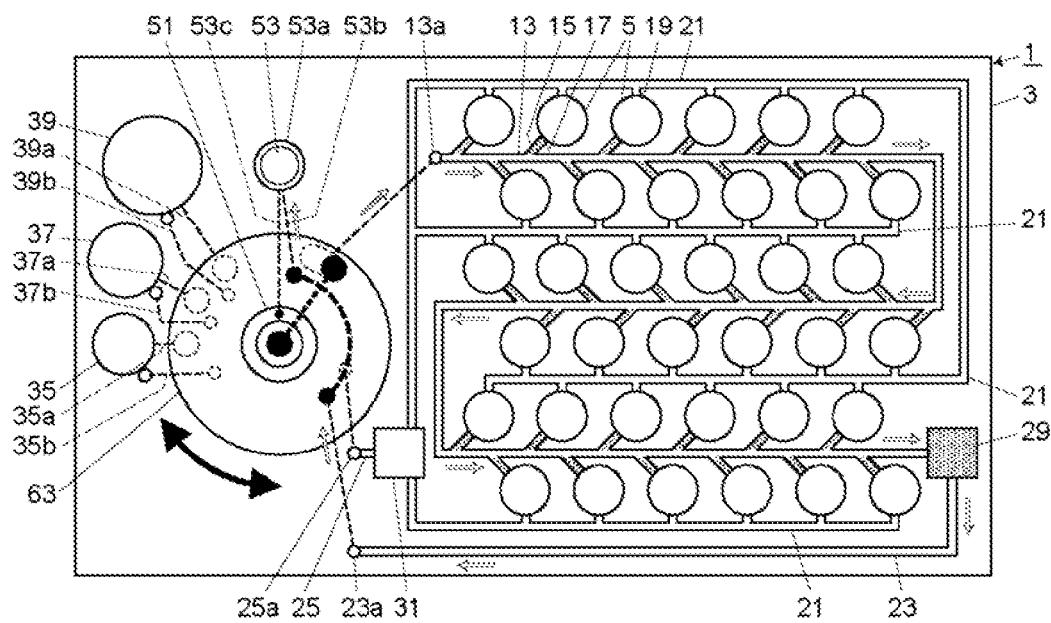
FIG. 12 is a plan view for explaining operation carried out subsequently to the operation shown in FIG. 11.

As shown in FIG. 12, the switching valve 63 is rotated to connect the flow channel 13a to the syringe flow channel 51c and to connect the flow channels 23a and 25a to the air drain flow channel 53b to establish the same connections as shown in FIG. 10. The syringe 51 is operated in its discharge direction to feed the gas contained in the flow channel of the switching valve 63, the syringe flow channel 51c, and the syringe 51 into the main flow channel 13 to purge the diluted sample mixture from the main flow channel 13 (see open arrows in FIG. 12). Under the purge pressure at which the diluted sample mixture is purged from the main flow channel 13, the injection flow channel 17 does not allow the diluted sample mixture to pass through it, and therefore, the diluted sample mixture still remains in the measuring flow channels 15 (see fine dots in FIG. 12). The diluted sample mixture purged from the main flow channel 13 is introduced into the liquid drain space 29, and therefore, the gas contained in the flow channels between the liquid drain space 29 and the bellows 53 is sequentially transferred toward the bellows 53 (see open arrows in FIG. 12). As a result, the bellows 53 expands.

Figure 13:
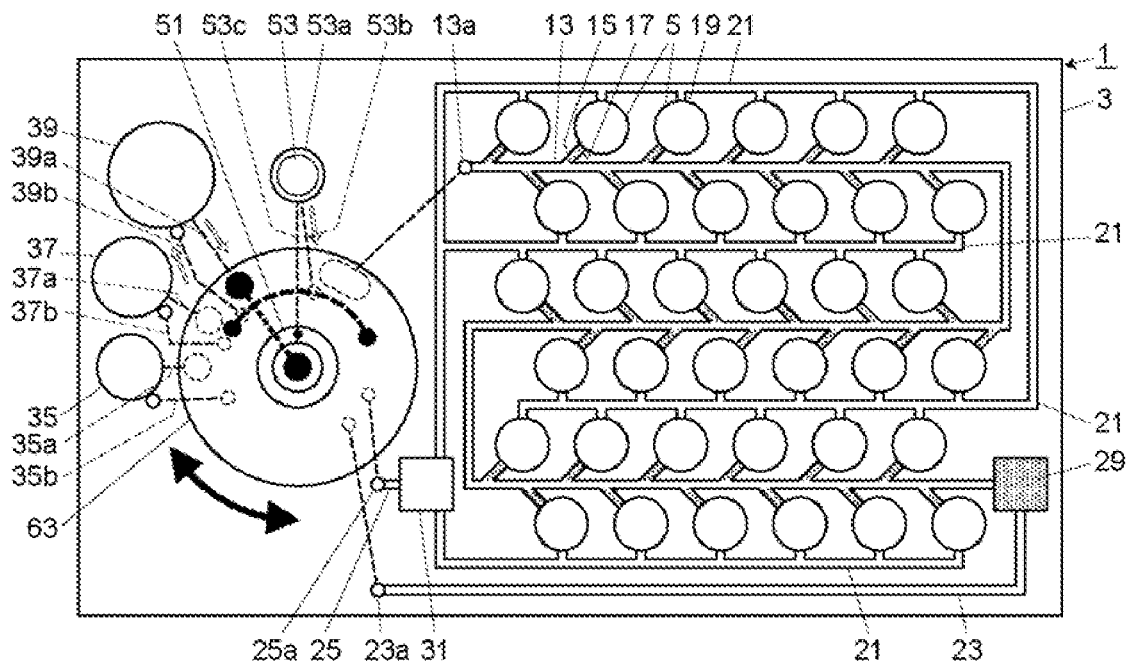
FIG. 13 is a plan view for explaining operation carried out subsequently to the operation shown in FIG. 12.

As shown in FIG. 13, the switching valve 63 is rotated to connect the air suction flow channel 39a to the syringe flow channel 51c and to connect the air suction container air drain flow channel 39b to the air drain flow channel 53b to establish the same connections as shown in FIG. 11. The syringe 51 is operated in its suction direction to suck a gas from the air suction container 39 into the flow channel of the switching valve 63, the syringe flow channel 51c, and the syringe 51. At this time, the bellows 53 contracts (see open arrows in FIG. 13) as in the case of the operation step described above with reference to FIG. 11.

Figure 14:
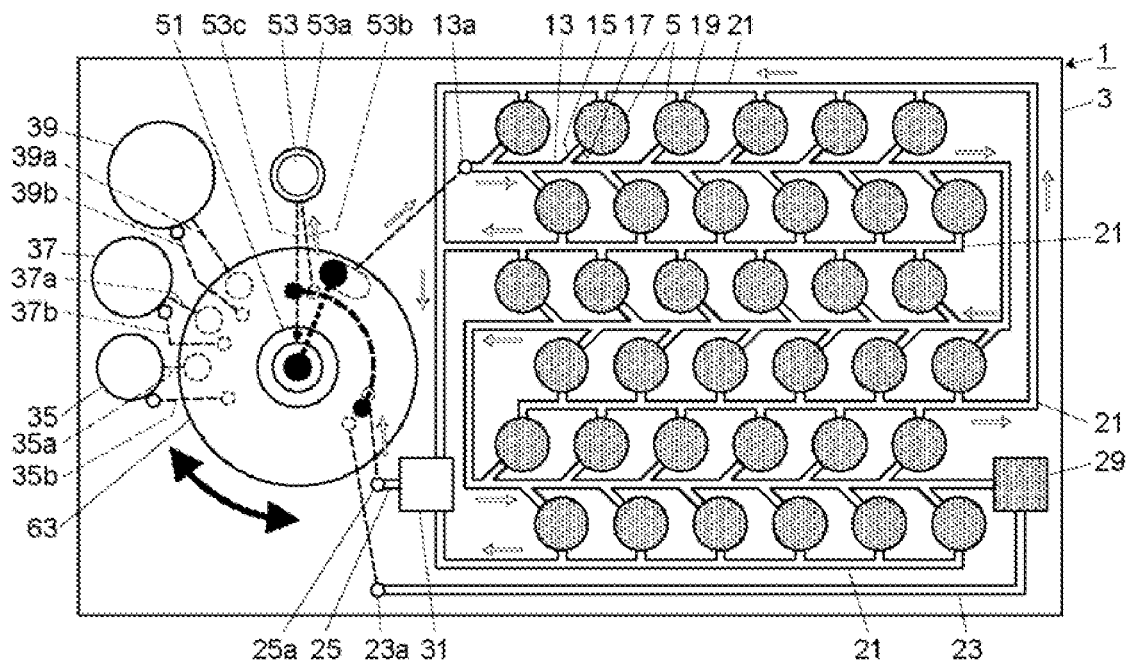
FIG. 14 is a plan view for explaining operation carried out subsequently to the operation shown in FIG. 13.

As shown in FIG. 14, the switching valve 63 is rotated to connect the flow channel 13a to the syringe flow channel 51c and to connect the flow channel 25a to the air drain flow channel 53b. This connection state is different from those shown in FIGS. 10 and 12 in that the liquid drain space 29, which is connected to the downstream side end of the main flow channel 13, is not connected to the flow channel of the switching valve 63. The syringe 51 is operated in its discharge direction. As described above, since the downstream side end of the main flow channel 13 is not connected to the bellows 53, a pressure higher than the liquid introduction pressure and the purge pressure is applied to the inside of the main flow channel 13. As a result, the diluted sample mixture contained in the measuring flow channels 15 is injected into the reactors 5 through the injection flow channels 17. After the diluted sample mixture is injected into the reactors 5, part of the gas contained in the main flow channel 13 flows into the reactors 5 through the measuring flow channels 15 and the injection flow channels 17. At this time, since the reactors 5 are in communication with the bellows 53 through the flow channels 19 and 21, the air drain space 31, the flow channel 25a and the air drain flow channel 53b, the gas contained in the flow channels between the reactors 5 and the bellows 53 is sequentially transferred toward the bellows 53 (see open arrows in FIG. 14). As a result, the bellows 53 expands.

The switching valve 63 is returned to its initial state shown in FIG. 1 to hermetically seal the containers, flow channels and drain spaces of the reactor plate 1. Then, the reactors 5 are heated by the temperature control system 67 to melt the wax 9. As a result, the diluted sample mixture injected into each of the reactors 5 sinks below the surface of the wax 9, and then the diluted sample mixture is mixed and reacted with the reagent 7. As has been described above, the use of the reactor plate 1 makes it possible to treat reaction in a closed system.

The reactors 5 may be heated by the temperature control system 67 before the diluted sample mixture is injected into the reactors 5 so that the wax 9 is melted before the diluted sample mixture is injected into the reactors 5. In this case, the diluted sample mixture injected into the reactors 5 immediately sinks below the surface of the wax 9 and is mixed and reacted with the reagent 7. Even when the switching valve 63 is in the connection state shown in FIG. 14, a closed system is ensured by the bellows 53. The containers, flow channels and drain spaces of the reactor plate 1 can be hermetically sealed by returning the switching valve 63 to its initial state shown in FIG. 1 after the diluted sample mixture is injected into the reactors 5. In this regard, it is to be noted that the switching valve 63 may be returned to its initial state shown in FIG. 1 at any time from just after the injection of the diluted sample mixture until the end of the reaction between the diluted sample mixture and the reagent 7, or after the completion of the reaction between the diluted sample mixture and the reagent 7.

As has been described above, the use of the reactor plate 1 makes it possible to treat reaction in a closed system, and also makes it possible to achieve a closed system also before and after reaction treatment.

According to the first embodiment of the present invention, the grooves constituting the flow channels 13, 15, 17, 19, 21 and 23 are formed in the flow channel base 11, but the present invention is not limited to this embodiment. For example, grooves constituting all or some of these flow channels may be formed in the surface of the container base 3.

Figure 15:
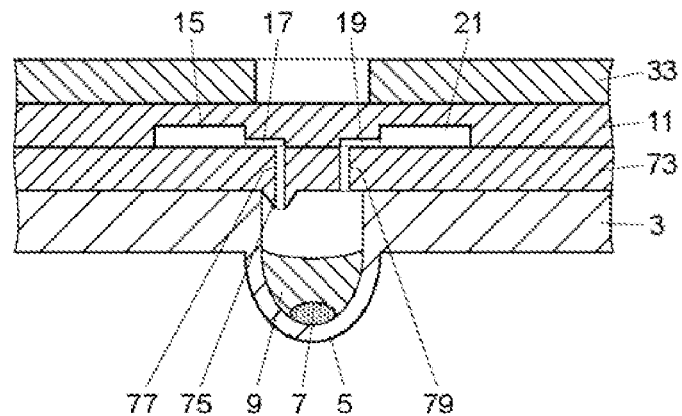
FIG. 15 is a partially-enlarged sectional view schematically showing a reactor and its vicinity of a reactor plate according to a second embodiment of the present invention.

FIG. 15 is a partially-enlarged sectional view schematically showing a reactor and its vicinity of a reactor plate according to a second embodiment of the present invention. The reactor plate according to the second embodiment of the present invention has the same structure as the reactor plate according to the first embodiment of the present invention described above with reference to FIGS. 1A to 14 except that a flow channel spacer is provided between the container base and the flow channel base.

More specifically, a flow channel spacer 73 is provided on the container base 3 so as to cover the reactor 5 arrangement region, and the flow channel base 11 and the flow channel cover 33 are further provided on the flow channel space 73 in the order listed. The flow channel spacer 73 is made of, for example, PDMS or silicone rubber. The thickness of the flow channel spacer 73 is in the range of, for example, 0.5 to 5.0 mm. The flow channel spacer 73 has a plurality of projections 75 each projecting into the reactor 5. The projection 75 has a substantially trapezoidal cross-section whose proximal end width is in the range of, for example, 1.0 to 2.8 mm and distal end width is in the range of, for example, 0.2 to 0.5 mm. That is, the projection 75 has a proximal end and a distal end narrower than the proximal end. Further, the projection 75 has a super-water-repellent surface. However, the projection 75 does not always need to have a water repellent surface.

The flow channel spacer 73 has a plurality of injection flow channels 77 each provided at a position corresponding to the projection 75 and constituted from a through hole extending from the distal end of the projection 75 to the surface of the flow channel space 73 located on the opposite side from the projection 75. The injection flow channel 77 has an inner diameter of, for example, 500 μm. An opening of the injection flow channel 77 located on the flow channel base 11 side is connected to the injection flow channel 17 provided in the flow channel base 11. It is to be noted that the reactor plate according to the second embodiment of the present invention is different from the reactor plate according to the first embodiment of the present invention described above with reference to FIGS. 1A to 14 in that the flow channel base 11 does not have recesses 27.

The flow channel spacer 73 also has a plurality of reactor air drain flow channels 79 each constituted from a through hole to bring the flow channel 19 provided in the flow channel base 11 into communication with the reactor 5.

Although not shown in the drawing, the flow channel spacer 73 has through holes at both ends of the main flow channel 13, at one end of the flow channel 21 located on the air drain space 31 side, and at both ends of the flow channels 23 and 25 to connect the flow channels 13, 21, 23, and 25 to the container 29 or 31 and/or the flow channel 23a or 25a provided in the container base 3.

According to the second embodiment of the present invention, the end of the injection flow channel 77 located on the opposite side from the injection flow channel 17 (i.e., the other end of the injection flow channel) is arranged at the tip of the projection 75 projecting from the upper surface of the reactor 5 into the reactor 5, and therefore, it is easy to drop a liquid into the reactor 5 when the liquid is injected into the reactor 5 through the injection flow channels 17 and 77.

By allowing the tip of the projection 75 to be located close to the side wall of the reactor 5 so that when a liquid passed through the injection flow channel 77 is discharged from the tip of the projection 75, liquid droplets formed at the tip of the projection 75 can be brought into contact with the side wall of the reactor 5, it is possible to inject the liquid into the reactor 5 through the side wall thereof, and thereby, to more reliably inject the liquid into the reactor 5. However, the projection 75 may be formed at such a position that liquid droplets formed at the tip of the projection 75 are not brought into contact with the side wall of the reactor 5.

Figure 16:
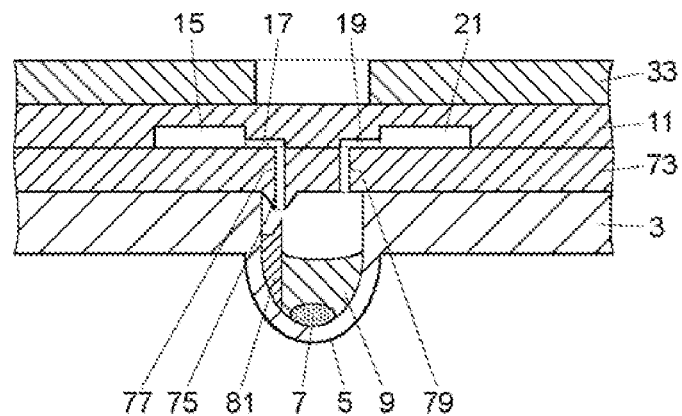
FIG. 16 is a partially-enlarged sectional view schematically showing a reactor and its vicinity of a reactor plate according to a third embodiment of the present invention.

FIG. 16 is a partially-enlarged sectional view schematically showing a reactor and its vicinity of a reactor plate according to a third embodiment of the present invention.

The reactor plate according to the third embodiment of the present invention is different from the reactor plate according to the second embodiment of the present invention described above with reference to FIG. 15 in that a projection 81 is further provided inside the reactor 5. The tip of the projection 81 is located under the tip of the projection 75. By providing such a projection 81, it becomes easy to guide liquid droplets formed at the tip of the projection 75 into the reactor 5. Such an effect becomes particularly effective by subjecting at least the tip surface of the projection 81 to hydrophilization treatment.

Figure 17:
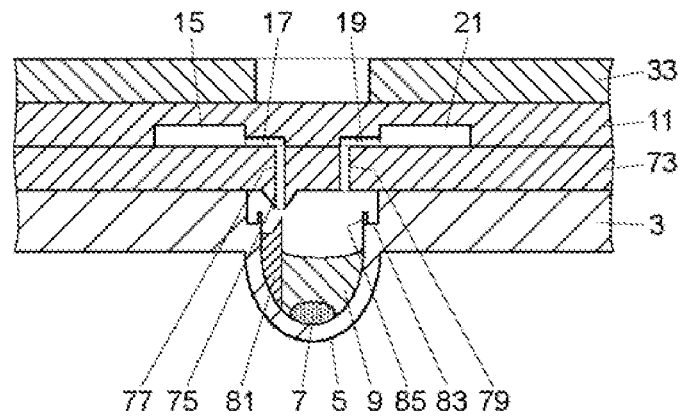
FIG. 17 is a partially-enlarged sectional view schematically showing a reactor and its vicinity of a reactor plate according to a fourth embodiment of the present invention.

FIG. 17 is a partially-enlarged sectional view schematically showing a reactor and its vicinity of a reactor plate according to a fourth embodiment of the present invention.

The reactor plate according to the fourth embodiment of the present invention is different from the reactor plate according to the third embodiment of the present invention described above with reference to FIG. 16 in that a stepped portion 83 and a projected rim 85 are further provided in the reactor 5. The stepped portion 83 is provided in the side wall of the reactor 5, and the projected rim 85 is provided on the upper surface of the stepped portion 83 so that space is left between the tip of the projected rim 185 and the upper surface of the reactor 5. The stepped portion 83 and the projected rim 85 have an annular shape when seen from above. Further, the projected rim 85 is provided so that space is left between the tip of the projected rim 85 and the side wall of the reactor 5.

By providing the projected rim 85 so that space is left between the tip of the projected rim 85 and the upper surface of the reactor 5 and between the tip of the projected rim 85 and the side wall of the reactor 5, it is possible to prevent a liquid contained in the reactor 5 from reaching the upper surface of the reactor 5 through the side wall of the reactor 5. Such an effect becomes particularly effective by subjecting at least the tip portion of the projected rim 85 to water repellent treatment.

Such a structure having the stepped portion 83 and the projected rim 85 as shown in FIG. 17 can be applied also to the embodiment shown in FIG. 15.

In each of the embodiments described above with reference to FIGS. 15, 16, and 17, grooves constituting the flow channels 13, 15, 17, 19, 21 and 23 are formed in the flow channel base 11, but the present invention is not limited to these embodiments. For example, grooves constituting all or some of these flow channels may be formed in any of the surface of the flow channel spacer 73 located on the flow channel base 11 side, the surface of the flow channel spacer 73 located on the container base 3 side, and the surface of the container base 3.

Part of the cylinder 51a of the syringe 51 may be formed from part of the switching valve 63.

Figure 18A:
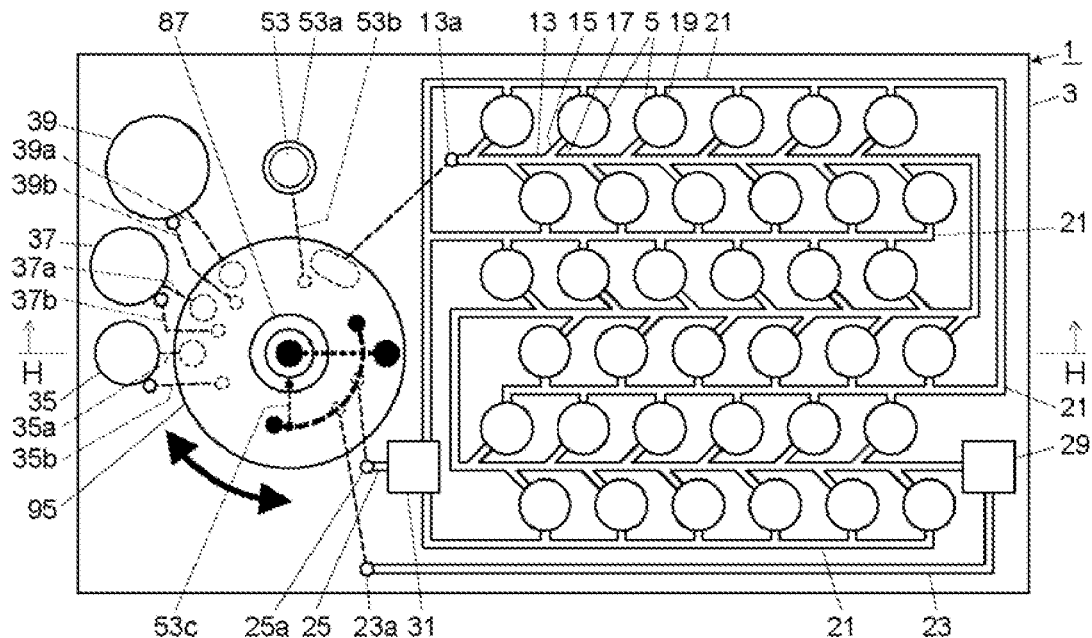
FIG. 18A is a schematic plan view of a reactor plate according to a fifth embodiment of the present invention.
Figure 18B:
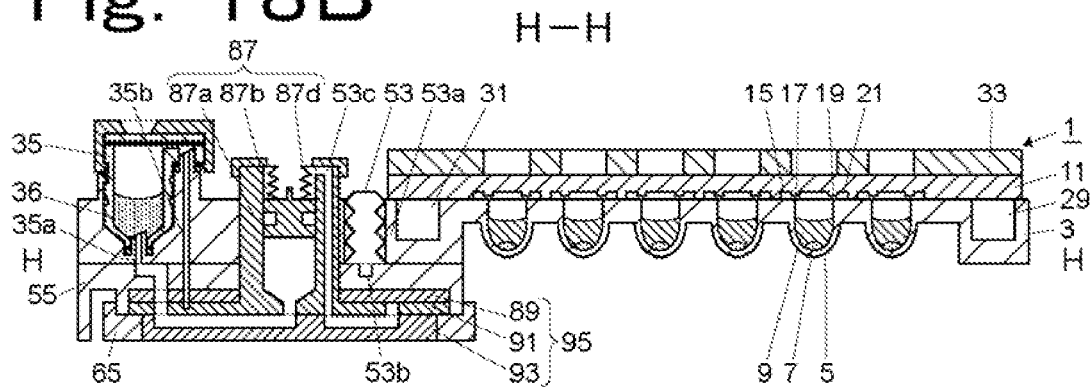
FIG. 18B is a schematic sectional view taken along the H-H line in FIG. 18A.
Figure 18C:
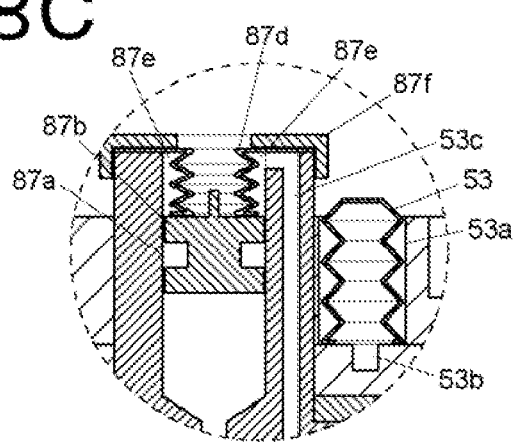
FIG. 18C is a partially-enlarged sectional view schematically showing a syringe, a bellows, and their vicinity of the reactor plate according to the fifth embodiment of the present invention.
Figure 19A:
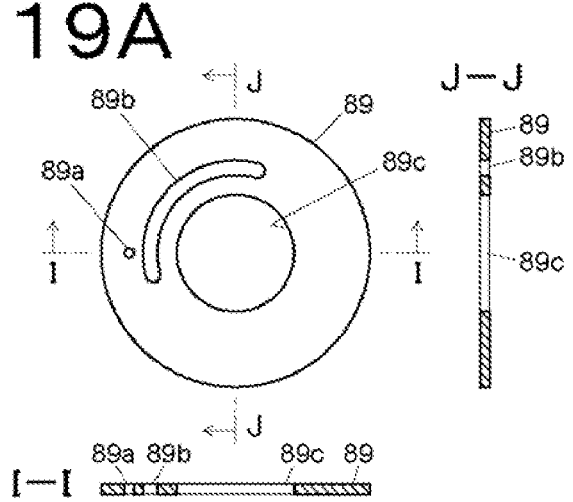
FIG. 19A shows a schematic plan view and schematic sectional views of a sealing plate of a switching valve of the reactor plate according to the fifth embodiment of the present invention.
Figure 19B:
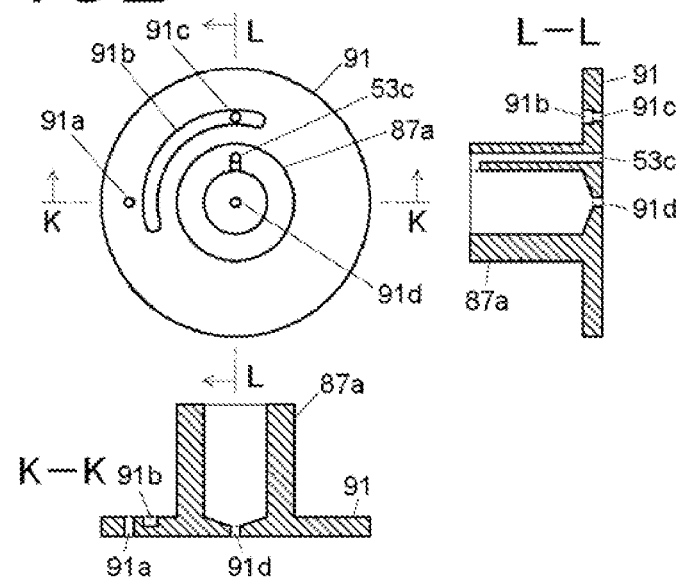
FIG. 19B shows a schematic plan view and schematic sectional views of a rotor upper plate of the switching valve.
Figure 19C:
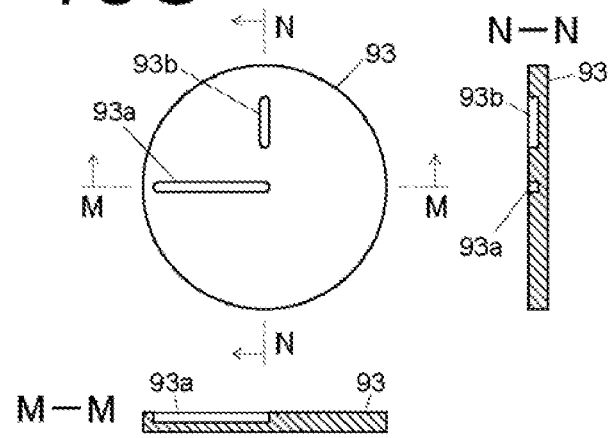
FIG. 19C shows a schematic plan view and schematic sectional views of a rotor base of the switching valve.

FIGS. 18A to 18C show a reactor plate according to a fifth embodiment of the present invention. More specifically, FIG. 18A is a schematic plan view of the reactor according to the fifth embodiment of the present invention, FIG. 18B is a schematic sectional view taken along the H-H line in FIG. 18A and further showing the measuring flow channels 15, the injection flow channels 17, the flow channels 19 and 21, the liquid drain space 29, the air drain space 31 and the bellows 53, and FIG. 18C is a partially-enlarged sectional view schematically showing the syringe 51, the bellows 53 and their vicinity. FIGS. 19A to 19C are schematic exploded views of a switching valve. More specifically, FIG. 19A shows a plan view and sectional views of a sealing plate, FIG. 19B shows a plan view and sectional views of a rotor upper plate, and FIG. 19C shows a plan view and sectional views of a rotor base.

According to the fifth embodiment of the present invention, a cylinder 87a of a syringe 87 is made of a resin material such as polypropylene or polycarbonate, and is integrally-molded with a rotor upper plate 91 of a switching valve 95.

The syringe 87 is constituted from the cylinder 87a, a plunger 87b and a cover body 87d. The cylinder 87a is arranged in a through hole provided in the container base 3 and the container bottom 55, and the plunger 87b is arranged in the cylinder 87a.

The cover body 87d has flexibility in the sliding direction of the plunger 87b, and is connected to the cylinder 87a and the plunger 87b. The cover body 87d is provided to create a sealed space 87e to cut off the inner wall of the cylinder 87a to be brought into contact with the plunger 87b from an atmosphere outside the cylinder 87a while keeping the airtightness. The sealed space 87e is a space enclosed with the cylinder 87a, the plunger 87b, and the cover body 87d.

The end of the cover body 87d connected to the cylinder 87a is fixed to the upper end of the cylinder 87a by a cylinder cap 87f so that the airtightness of the sealed space 87e can be ensured. The other end of the cover body 87d is connected to the upper surface of the plunger 87b using an adhesive so that the airtightness of the sealed space 87e can be ensured. However, a method for connecting the cover body 87d to the cylinder 87a and the plunger 87b is not limited to the method described above, and the connecting positions of the cover body 87d are not limited to those described above. Further, the plunger and the cover body may be integrally molded. The plunger and the cover body can be integrally molded using, for example, silicone rubber.

As described above, since the cover body 87d is connected to the cylinder 87a and the plunger 87b to create a sealed space 87e enclosed with them, the entry of foreign matter from the outside and the leakage of a liquid to the outside through a gap between the cylinder 87a and the plunger 87b do not occur, thereby preventing the pollution of an environment outside the reactor plate. It is to be noted that as described above, since the cover body 87d has flexibility in the sliding direction of the plunger 87b, the plunger 87b can be slidably operated.

Hereinbelow, the syringe air drain flow channel 53c and the switching valve 95 will be described with reference to FIGS. 19A to 19C as well as FIGS. 18A to 18C.

The switching valve 95 is constituted from a disk-shaped sealing plate 89, rotor upper plate 91, and rotor base 93. The switching valve 95 is attached to the container bottom 55 by means of a lock 65.

The sealing plate 89 has a through hole 89a provided in the vicinity of the peripheral portion thereof, a through groove 89b provided on a concentric circle thereof closer to the center thereof than the through hole 89a, and a through hole 89c provided at the center thereof to insert the cylinder 87a. The through hole 89a is to be connected to any of the flow channels 13a, 35a, 37a and 39a, and the through groove 89b is to be connected to at least two of the flow channels 23a, 25a, 35b, 37b, 39b and 53b. On the surface of the sealing plate 89 to be opposed to the container bottom 55, a fluorocarbon resin layer (not shown) is provided.

The rotor upper plate 91 has a cylindrical cylinder 87a, a through hole 91a, a groove 91b, a through hole 91c, and a through hole 91d. The cylinder 87a is provided on one surface of the rotor upper plate 91 so as to be located at the center thereof, the through hole 91a is provided at a position corresponding to the through hole 89a of the sealing plate 89, the groove 91b is provided in the surface of the rotor upper plate 91 so as to correspond to the through groove 89b of the sealing plate 89, the through hole 91c is provided in the groove 91b, and the through hole 91d is provided at the center of the rotor upper plate 91. The through hole 91d is located at the bottom of the cylinder 87a and constitutes a discharge port of the cylinder 87a.

The rotor upper plate 91 also has a syringe air drain flow channel 53c constituted from a through hole extending from the upper end surface of the cylinder 87a to the back surface of the rotor upper plate 91. In the upper end surface of the cylinder 87a, a notch extending from the inner wall of the cylinder 87a to the syringe air drain flow channel 53c is provided. As shown in FIG. 18C, this notch allows the sealed space 87e to communicate with the syringe air drain flow channel 53c in a state where the upper end surface of the cylinder 87a is covered with the cover body 87d.

The rotor base 93 has a groove 93a and a groove 93b in its surface to be brought into contact with the back surface of the rotor upper plate 91. The groove 93a is provided to connect the through hole 91a and the through hole 91d provided in the rotor upper plate 91, and the groove 93b is provided to connect together the syringe air drain flow channel 53c and the through hole 91c provided in the rotor upper plate 91.

As shown in FIG. 18B, the sealing plate 89, the rotor upper plate 91 and the rotor base 93 constituting the switching valve 95 are superposed so that the cylinder 87a is inserted into the through hole 89c of the sealing plate 89.

The through hole 91d of the rotor upper plate 91 constituting a discharge port of the cylinder 87a is connected to the through hole 89a of the sealing plate 89 through the groove 93a of the rotor base 93 and the through hole 91a of the rotor upper plate 91.

The sealed space 87e (see FIG. 18C) is connected to the through groove 89b of the sealing plate 89 through the syringe air drain flow channel 53c, the groove 93b of the rotor base 93, and the through hole 91c and the through groove 91b of the rotor upper plate 91.

Hereinbelow, flow channel connection will be described with reference to FIGS. 18A to 18C and FIGS. 19A to 19C.

The through hole 91d of the rotor upper plate 91 constituting a discharge port of the cylinder 87a is connected to any of the flow channels 13a, 35a, 37a and 39a through the groove 93a and the through holes 91a, 89a by rotating the switching valve 95.

At the same time as the through hole 91d is connected to any of the flow channels 13a, 35a, 37a and 39a, the air drain flow channel 53b is connected to at least any of the flow channels 23a, 25a, 35b, 37b and 39b through the through grooves 89b and 91b. At this time, the sealed space 87e is connected to the air drain flow channel 53b through the cylinder air drain flow channel 53c, the groove 93b, the through hole 91c, and the through grooves 89b and 91b.

According to the fifth embodiment of the present invention, it is possible to eliminate a flow channel for connecting the syringe 87 to the switching valve 95, thereby simplifying the flow channel configuration of the reactor plate.

In general, in a case where a flow channel has a joint, there is a possibility that a liquid or gas will leak through the joint, or a liquid will be accumulated in the joint. However, according to the fifth embodiment of the present invention, since the cylinder 87a and the rotor upper plate 91 are integrally molded, there is no joint between the syringe 87 and the switching valve 95, and therefore, liquid leakage, gas leakage and liquid accumulation do not occur between the syringe 87 and the switching valve 95.

Further, in general, if liquid accumulation occurs in the joint of a flow channel, there is a fear of reduction in the volume of a liquid fed through the flow channel, carry-over of a liquid accumulated in the joint of the flow channel into another liquid fed through the flow channel or contamination of another liquid fed through the flow channel with a liquid accumulated in the joint of the flow channel, or fluctuation in the concentration of a liquid fed through the flow channel. However, according to the fifth embodiment of the present invention, since there is no joint between the syringe 87 and the switching valve 95, such a fear can be eliminated.

As shown in FIGS. 1B and 1C, in a case where the flow channel 51c is provided between the syringe 51 and the switching valve 63 to arrange the syringe above the switching valve, the cylinder 51a cannot be formed in a portion where the flow channel 51c is provided. However, since the reactor plate according to the fifth embodiment of the present invention shown in FIGS. 18A to 18C does not need to have a flow channel for connecting the syringe 87 and the switching valve 95, the capacity of the cylinder 87a can be made larger than that of the cylinder 51a even when the cylinder 51a and the cylinder 87a have the same two-dimensional size.

In a case where the cylinder 87a is formed to have the same capacity and two-dimensional size as the cylinder 51a, the level of the upper end surface of the cylinder 87a can be made lower than that of the cylinder 51a. On the other hand, in a case where the cylinder 87a is formed to have the same capacity and upper end surface level as the cylinder 51a, the two-dimensional size of the cylinder 87a can be made smaller than that of the cylinder 51a.

For example, even in a case where the upper end surface of the cylinder 51a needs to be located at a higher level than the upper surface of the entire reactor plate 1 due to limitations on the two-dimensional size of the entire reactor plate 1, since the level of the upper end surface of the cylinder 87a can be made lower than that of the cylinder 51a while the capacity and two-dimensional size of the cylinder 87a remain the same as the cylinder 51a, it is possible to allow the upper end surface of the cylinder 87a to be located at the same or lower level than the upper surface of the entire reactor plate 1. This makes it possible to eliminate problems caused by the cylinder whose upper end surface is located at a higher level than the upper surface of the entire reactor plate, such as difficulty in stacking the two or more reactor plates on top of each other for storage and increase in the size of a package of the reactor plate.

By making the two-dimensional size of the cylinder 87a smaller than that of the cylinder 51a while the capacity of the cylinder 87a remains the same as the cylinder 51a, it is possible to reduce the two-dimensional size of the entire reactor plate 1.

The present invention has been described above in detail with reference to some embodiments, but is not limited to these embodiments, and various changes can be made to the shape, material, arrangement, number and size of each of the components and the flow channel configuration of the reactor plate.

For example, the bellows 53 connected to the air drain flow channel 53b can have any structure as long as it is a variable volume member whose internal volume can be passively changed. Examples of such a structure include a bag-shaped one made of a flexible material and a syringe-type one.

The reactor plate according to the present invention does not always need to have a variable volume member such as a bellows 53.

In a case where the container 35, 37 or 39 does not previously contain a liquid such as a reagent, the air drain flow channel does not always need to have, as a part thereof, a flow channel 35e, 37e or 39e constituted from a narrow hole.

According to the above embodiments, the air drain flow channels 35b, 37b and 39b which are in communication with the containers 35, 37 and 39 as the sealed containers of the reactor plate, are connected to the air drain flow channel 53b through the switching valve 63, but may be directly connected to the outside of the reactor plate or a variable volume member such as the bellows 53.

Each of the containers 35, 37 and 39 may be sealed with an openable and closable cap.

According to the above embodiments, the container base 3 is formed from a single component, but may be formed from two or more components.

The reagent contained in the reactors 5 may be a dried reagent.

The sample container 35 and the reactors 5 do not always need to previously contain a reagent.

According to the above embodiments, the reagent container 37 contains dilution water 49, but may contain a reagent instead of the dilution water 49.

The container base 3 may include a gene amplification container for carrying out gene amplification reaction. For example, by allowing the reagent container 37 to be empty, the reagent container 37 may be used as a gene amplification container.

By allowing the reactors 5 to previously contain a reagent for gene amplification reaction, it is possible to carry out gene amplification reaction in the reactors 5.

In a case where a liquid to be introduced into the main flow channel 13 contains a gene, the reactors 5 may previously contain a probe which reacts with the gene.

According to the above embodiments, the syringe 51 is arranged above the switching valve 63, but the position of the syringe 51 is not limited to the position above the switching valve 63, and the syringe 51 can be arranged anywhere.

According to the above embodiments, the rotary switching valve 63 is used as a switching valve, but a switching valve to be used in the present invention is not limited thereto, and various flow channel switching valves can be used. The reactor plate according to the present invention may include two or more switching valves.

According to the above embodiments, a liquid contained in the measuring flow channels 15 is injected into the reactors 5 through the injection flow channels 17 by applying pressure to the inside of the main flow channel 13 after air purge, but the reaction treatment method according to the present invention is not limited thereto. For example, the flow channel configuration of the reactor plate according to the present invention may be changed so that a negative pressure can be created in the flow channel 21 by the syringe 51. In this case, a liquid contained in the measuring flow channels 15 can be injected into the reactors 5 through the injection flow channels 17 by creating a negative pressure in the flow channel 21 and then in the reactors 5. Alternatively, another syringe may be further prepared. In this case, a liquid contained in the measuring flow channels 15 can be injected into the reactors 5 by creating a positive pressure in the main flow channel 13 and a negative pressure in the reactors 5.

According to the above embodiments, the penetrable portions and second penetrable portions of the sealed containers are formed from films 35j, 35l, 37j, 37l, 39j and 39l made of, for example, aluminum, but are not limited to aluminum films. The penetrable portion and the second penetrable portion may be formed from films other than aluminum films, or may be made of the same material as the container main body. For example, in a case where the container main body is made of a resin material such as polypropylene or polycarbonate, the penetrable portion and the second penetrable portion may be integrally molded with the container main body so that the penetrable portion and second penetrable portion made of the resin material can have such a thickness that the projecting flow channel and the second projecting flow channel can penetrate them. In this regard, it is to be noted that when the penetrable portion and the second penetrable portion are integrally molded with the container main body, the thickness of each of the penetrable portion and the second penetrable portion is in the range of, for example, 0.01 to 0.5 mm.

According to the above embodiments, all the measuring flow channels 15 are connected to one main flow channel 13, but the flow channel configuration of the reactor plate according to the present invention is not limited thereto. For example, two or more main flow channels may be provided, and one or more measuring flow channels may be connected to each of the main flow channels.

The main flow channel of the reactor plate according to the present invention can be hermetically sealed, and an example of such a hermetically-sealable main flow channel includes a main flow channel whose both ends are openable and closable. The phrase "main flow channel whose both ends are openable and closable" includes a case where the end of the main flow channel is connected to another space whose end located on the opposite side from the main flow channel is openable and closable. For example, in the above embodiments, such 'another space' corresponds to the flow channel 13a, the liquid drain space 29, the flow channel 23, or the flow channel 23a.

The reactor air drain flow channel of the reactor plate according to the present invention can be hermetically sealed, and an example of such a hermetically-sealable reactor air drain flow channel includes a reactor air drain flow channel whose end located on the opposite side from the reactor is openable and closable. The phrase "reactor air drain flow channel whose end located on the opposite side from the reactor is openable and closable" includes a case where the end of the reactor air drain flow channel located on the opposite side of the reactor is connected to another space whose end located on the opposite side of the reactor air drain flow channel is openable and closable. For example, in the above embodiments, such another space corresponds to the air drain space 31, the flow channel 25, or the flow channel 25a.

According to such an embodiment, a liquid is introduced into the main flow channel and the measuring flow channels, and the liquid is purged from the main flow channel, and the liquid remaining in the measuring flow channels is injected into the reactors, and finally the both ends of the main flow channel and the end of the reactor air drain flow channel located on the opposite side from the reactor are closed to hermetically seal the main flow channel and the reactor air drain flow channel.

What is claimed is:

1. A reactor plate comprising:
   a sealed reactor;
   a reactor flow channel connected to the reactor;
   a sealed container provided separately from the reactor and containing a liquid;
   a sealed container flow channel to be connected to the sealed container;
   a syringe for sending a liquid;
   a switching valve for connecting the syringe to the reactor flow channel or the sealed container flow channel;
   a projecting flow channel connected to an end of the sealed container flow channel located on the sealed container side;
   a sealed container air drain flow channel to be connected to the sealed container; and
   a second projecting flow channel connected to the end of the sealed container air drain flow channel located on the sealed container side,
   wherein the sealed container has a penetrable portion through which the projecting flow channel can penetrate, the penetrable portion being provided to be opposed to the projecting flow channel and being located at such a position that the projecting flow channel penetrating the penetrable portion is brought into contact with a liquid contained in the sealed container,
   whereby the sealed container can be connected to the sealed container flow channel by inserting the tip of the projecting flow channel into the sealed container through the penetrable portion,
   wherein the sealed container further has a second penetrable portion through which the second projecting flow channel can penetrate, the second penetrable portion being provided to be opposed to the second projecting flow channel and being located at a position such that the second projecting flow channel penetrating the second penetrable portion is inserted into a space in the sealed container but is not brought into contact with a liquid contained in the sealed container,
   whereby an air space in the sealed container can be connected to the sealed container air drain flow channel by inserting the tip of the second projecting flow channel into the sealed container through the second penetrable portion.

2. The reactor plate according to claim 1, comprising two or more sets of the sealed container, the sealed container flow channel and the projecting flow channel,
   wherein the switching valve can connect the syringe to any of the sealed container flow channels.

3. The reactor plate according to claim 1, further comprising a sealed container holding system for holding the sealed container at a first and second holding positions,
   the first holding position being such that the penetrable portion and the projecting flow channel are opposed to each other, and
   the second holding position being such that the tip of the projecting flow channel is inserted into the sealed container through the penetrable portion.

4. The reactor plate according to claim 1, wherein the sealed container has:
   a sealed container main space having the penetrable portion through which the projecting flow channel of the sealed container flow channel can penetrate;
   a sealed container air drain space being provided separately from the sealed container main space and serving as an air space to be connected to the sealed container air drain flow channel; and
   a communicating flow channel being provided at a position higher than the level of a liquid contained in the sealed container main space to connect together the sealed container main space and the sealed container air drain space.

5. The reactor plate according to claim 4, wherein the sealed container air drain space has an inner diameter of 3 mm or less.

6. The reactor plate according to claim 1, comprising two or more sets of the sealed container, the sealed container flow channel, the projecting flow channel, the sealed container air drain flow channel, and the second projecting flow channel,
   wherein the switching valve can connect the syringe to any of the sealed container flow channels.

7. The reactor plate according to claim 1, further comprising a sealed container holding system for holding the sealed container at first and second holding positions,
   the first holding position being such that the penetrable portion and the projecting flow channel are opposed to each other, and the second penetrable portion and the second projecting flow channel are opposed to each other, and
   the second holding position being such that the tip of the projecting flow channel is inserted into the sealed container through the penetrable portion, and the tip of the second projecting flow channel is inserted into the sealed container through the second penetrable portion.

8. The reactor plate according to claim 1, wherein the sealed container includes a sample container for receiving a sample liquid.

9. The reactor plate according to claim 8, wherein the sample container has an upper opening hermetically sealed with an elastic member through which a sharp-tipped dispensing tool can penetrate to form a through hole closable by pulling out the dispensing tool due to its elasticity.

10. The reactor plate according to claim 8, wherein the sample container has an upper opening hermetically sealed with an elastic member having a cut openable by inserting a sample dispensing tool and closable by pulling out the sample dispensing tool due to its elasticity so that the upper opening can be hermetically sealed again.

11. The reactor plate according to claim 8, wherein the sample container previously contains a sample pretreatment solution or a reagent.

12. The reactor plate according to claim 1, further comprising a gene amplification container for carrying out gene amplification reaction, the gene amplification container being constituted from the sealed container.

13. The reactor plate according to claim 1, wherein the switching valve is a rotary valve.

14. The reactor plate according to claim 13, wherein the rotary valve has a port to be connected to the syringe at a rotational center thereof, and the syringe is arranged on or above the rotary valve.

15. The reactor plate according to claim 1, further comprising a reactor air drain flow channel connected to the reactor,
wherein the reactor flow channel is constituted from a groove formed in a contact surface between two substrates bonded together or from the groove and a through hole formed in the substrate, and the reactor flow channel has a main flow channel to be connected to the syringe, a measuring flow channel having a predetermined capacity and branching off from the main flow channel, and an injection flow channel whose one end is connected to the measuring flow channel and other end is connected to the reactor,
wherein the main flow channel and the reactor air drain flow channel can be hermetically sealed, and
wherein the injection flow channel is narrower than the measuring flow channel in such a way that the injection flow channel does not allow a liquid to pass through it under a liquid introduction pressure at which the liquid is introduced into the main flow channel and the measuring flow channel, and under a purge pressure at which the liquid is purged from the main flow channel but allows the liquid to pass through it under a pressure higher than the liquid introduction pressure and the purge pressure.

16. The reactor plate according to claim 15, wherein the contact angle of a water droplet on the injection flow channel surface is 90° or more, and the area of the interface between the injection flow channel and the measuring flow channel is in the range of 1 to 10,000,000 $\mu m^2$.

17. The reactor plate according to claim 15, comprising the two or more reactors,
wherein the measuring flow channel and the injection flow channel are provided for each of the reactors, and
wherein the two or more measuring flow channels are connected to the main flow channel.

18. The reactor plate according to claim 15, wherein the other end of the injection flow channel is located at the tip of a projection projecting from the upper surface of the reactor into the reactor, and the projection has a proximal end and a distal end narrower than the proximal end.

19. The reactor plate according to claim 1, wherein the reactor is used for carrying out at least any of color reaction, enzyme reaction, and fluorescence, chemiluminescence, or bioluminescence reaction.

20. The reactor plate according to claim 1, the reactor plate being designed to measure a gene-containing sample,
wherein the sealed container or the reactor is used to carry out gene amplification reaction.

21. The reactor plate according to claim 1, wherein the reactor is made of an optically-transparent material so that optical measurement can be carried out from the top or bottom side of the reactor.

22. The reactor plate according to claim 1, wherein when a liquid to be injected into the reactor contains a gene, the reactor contains a probe which reacts with the gene.

23. A reaction treatment method using the reactor plate according to claim 15, comprising the steps of:
filling the main flow channel and the measuring flow channel with a liquid under the liquid introduction pressure;
allowing a gas to flow through the main flow channel to purge the liquid from the main flow channel while the liquid contained in the measuring flow channel is left as it is; and
injecting the liquid contained in the measuring flow channel into the reactor through the injection flow channel by creating a positive pressure much higher than the liquid introduction pressure in the main flow channel and/or creating a negative pressure in the reactor.

* * * * *